(12) United States Patent
Kirschman

(10) Patent No.: US 11,185,457 B2
(45) Date of Patent: *Nov. 30, 2021

(54) MEDICAL AIR TREATMENT DEVICE

(71) Applicant: David Louis Kirschman, Dayton, OH (US)

(72) Inventor: David Louis Kirschman, Dayton, OH (US)

(73) Assignee: Aerobiotix, Inc., Miamisburg, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/854,026

(22) Filed: Apr. 21, 2020

(65) Prior Publication Data
US 2020/0261295 A1 Aug. 20, 2020

Related U.S. Application Data

(63) Continuation of application No. 15/813,548, filed on Nov. 15, 2017, now Pat. No. 10,702,435.
(Continued)

(51) Int. Cl.
*B01D 46/00* (2006.01)
*A61G 13/10* (2006.01)
(Continued)

(52) U.S. Cl.
CPC ............ *A61G 13/108* (2013.01); *A61L 9/015* (2013.01); *A61L 9/20* (2013.01); *A61M 1/784* (2021.05); *B01D 46/0028* (2013.01); *B01D 46/0041* (2013.01); *F24F 3/16* (2013.01); *A61L 2209/11* (2013.01); *A61L 2209/12* (2013.01); *A61L 2209/134* (2013.01); *A61L 2209/14* (2013.01); *A61L 2209/16* (2013.01);
(Continued)

(58) Field of Classification Search
CPC ...... B01D 15/00; B01D 15/04; B01D 15/002; B01D 46/0028; B01D 46/0041; B01D 2279/40; F24F 3/16; F24F 3/1603; F24F 2221/22; F24F 2221/125; Y10S 55/18; A61L 9/20; A61L 9/015; A61L 2209/12; A61L 2209/14; A61L 2209/21; A61L 2209/11; A61L 2209/13; A61L 2209/16; A61G 13/108; A61M 1/0052; A61M 2205/07; A61M 2205/7518
USPC ... 55/385.2, 385.1, 356, 359, 471, 472, 486, 55/503; 96/417, 418, 223, 224; 454/187; 604/35, 45, 264; 95/273, 286
See application file for complete search history.

(56) References Cited

U.S. PATENT DOCUMENTS 3,768,970 A * 10/1973 Malmin .................... A61L 9/18
  96/224
3,812,370 A 5/1974 LaViolette
(Continued)

FOREIGN PATENT DOCUMENTS

WO       9428814      12/1994
WO    WO 9428814     12/1994

*Primary Examiner* — Minh Chau T Pham
(74) *Attorney, Agent, or Firm* — Jacox, Meckstroth & Jenkins

(57) ABSTRACT

An air treatment device having a flexible air hose, duct or gooseneck member. The air hose, duct or gooseneck member permits an inlet end thereof to be positioned in proximity to a patient so that a negative pressure can be created around the patient so that air can sucked or vacuumed into the system whereupon it is treated as the air flows through the system.

31 Claims, 19 Drawing Sheets

Related U.S. Application Data

(60) Provisional application No. 62/422,810, filed on Nov. 16, 2016.

(51) Int. Cl.
*A61M 1/00* (2006.01)
*A61L 9/015* (2006.01)
*A61L 9/20* (2006.01)
*F24F 3/16* (2021.01)

(52) U.S. Cl.
CPC ...... *A61L 2209/21* (2013.01); *A61M 2205/07* (2013.01); *A61M 2205/7518* (2013.01); *B01D 2279/40* (2013.01)

(56) References Cited

U.S. PATENT DOCUMENTS

| | | | |
|---|---|---|---|
| 3,988,131 A | 10/1976 | Kanazawa et al. | |
| 4,118,191 A | 10/1978 | Bohnensieker | |
| 4,163,650 A | 8/1979 | Watson et al. | |
| 4,210,429 A | 7/1980 | Golstein | |
| 4,244,710 A | 1/1981 | Burger | |
| 4,531,956 A | 7/1985 | Howorth | |
| 4,621,195 A | 11/1986 | Larsson | |
| 4,737,173 A | 4/1988 | Kudirka et al. | |
| 4,749,385 A | 6/1988 | Brunner et al. | |
| 4,787,922 A | 11/1988 | Kulitz | |
| 4,900,344 A | 2/1990 | Lansing | |
| 4,954,320 A | 9/1990 | Birmingham et al. | |
| 5,225,167 A | 7/1993 | Wetzel | |
| 5,233,975 A | 8/1993 | Choate | |
| 5,240,478 A | 8/1993 | Messina | |
| 5,281,246 A | 1/1994 | Ray et al. | |
| 5,399,319 A | 3/1995 | Schoenberger et al. | |
| 5,616,172 A | 4/1997 | Tuckerman et al. | |
| 5,656,242 A | 8/1997 | Morrow et al. | |
| 5,681,374 A | 10/1997 | Von Glehn | |
| 5,997,619 A | 12/1999 | Knuth et al. | |
| 6,099,607 A | 8/2000 | Haslebacher | |
| 6,110,259 A | 8/2000 | Schultz et al. | |
| 6,143,048 A | 11/2000 | Comproni et al. | |
| 6,322,614 B1 | 11/2001 | Tillmans | |
| 6,395,047 B1 | 5/2002 | Smith | |
| 6,607,573 B1 | 8/2003 | Chaurushia et al. | |
| 6,616,720 B1 | 9/2003 | Smith | |
| 7,531,141 B2 | 5/2009 | Descotes et al. | |
| 8,465,576 B2 * | 6/2013 | Della Valle | A61G 13/108 96/224 |
| 9,433,693 B2 | 9/2016 | Kirschman | |
| 9,457,119 B2 | 10/2016 | Kirschman | |
| 9,764,054 B2 | 9/2017 | Kirschman | |
| 10,702,435 B2 * | 7/2020 | Kirschman | A61L 9/20 |
| 2003/0150328 A1 | 8/2003 | Hansson et al. | |
| 2004/0020363 A1 | 2/2004 | LaFerriere et al. | |
| 2004/0047776 A1 | 3/2004 | Thomsen | |
| 2005/0229555 A1 | 10/2005 | Montgomery | |
| 2010/0115896 A1 | 5/2010 | Reid et al. | |
| 2010/0260644 A1 | 10/2010 | Day et al. | |
| 2012/0282135 A1 | 11/2012 | Trapani | |
| 2012/0313014 A1 | 12/2012 | Stibich et al. | |
| 2014/0157989 A1 * | 6/2014 | Kirschman | A61L 2/26 96/224 |
| 2014/0165842 A1 | 6/2014 | Bonano et al. | |
| 2016/0263267 A1 | 9/2016 | Kirschman | |
| 2017/0296691 A1 | 10/2017 | Kirschman | |
| 2019/0254903 A1 | 8/2019 | Hag | |

* cited by examiner

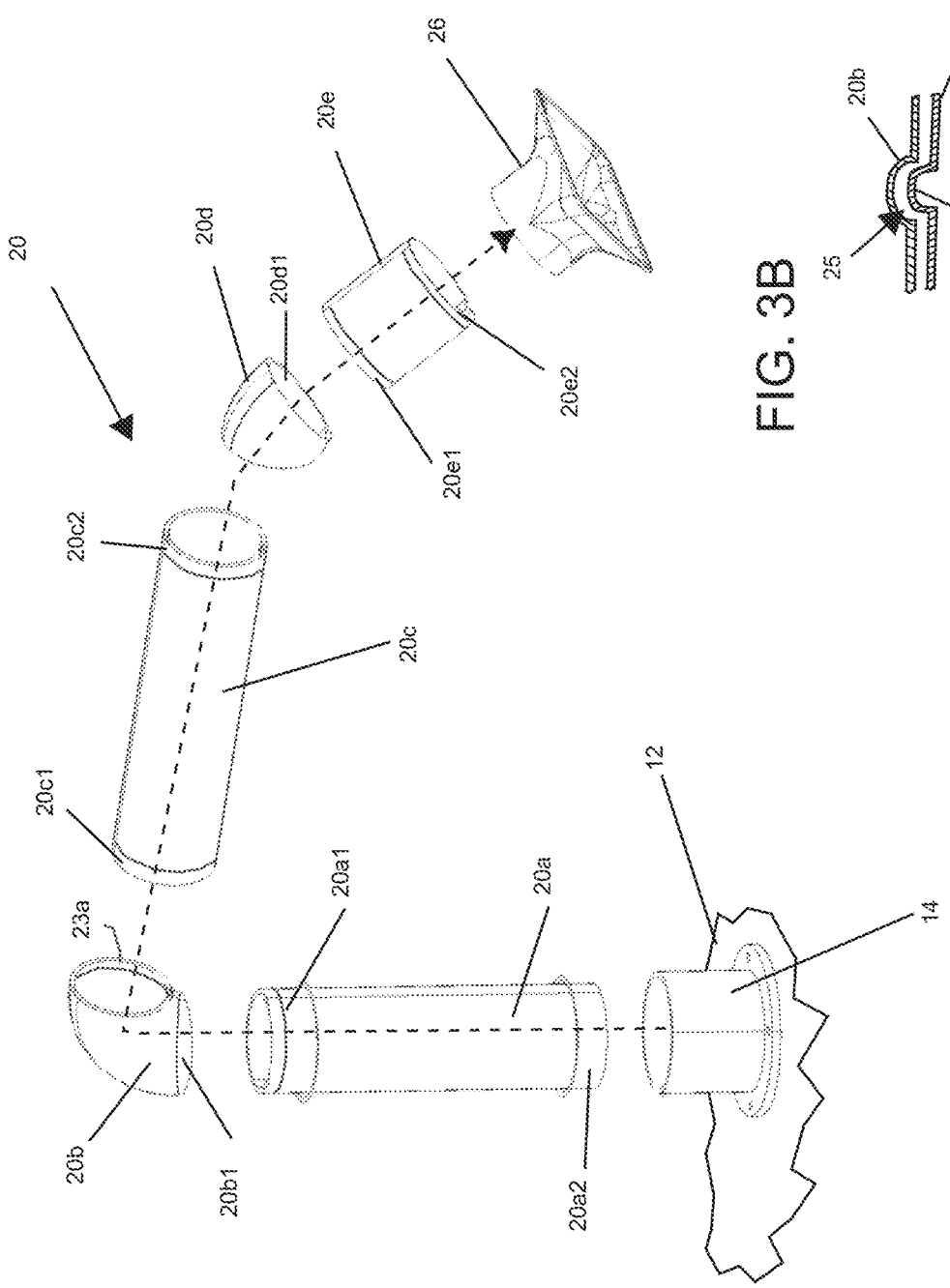
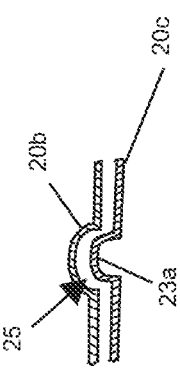
FIG. 3A
FIG. 3B

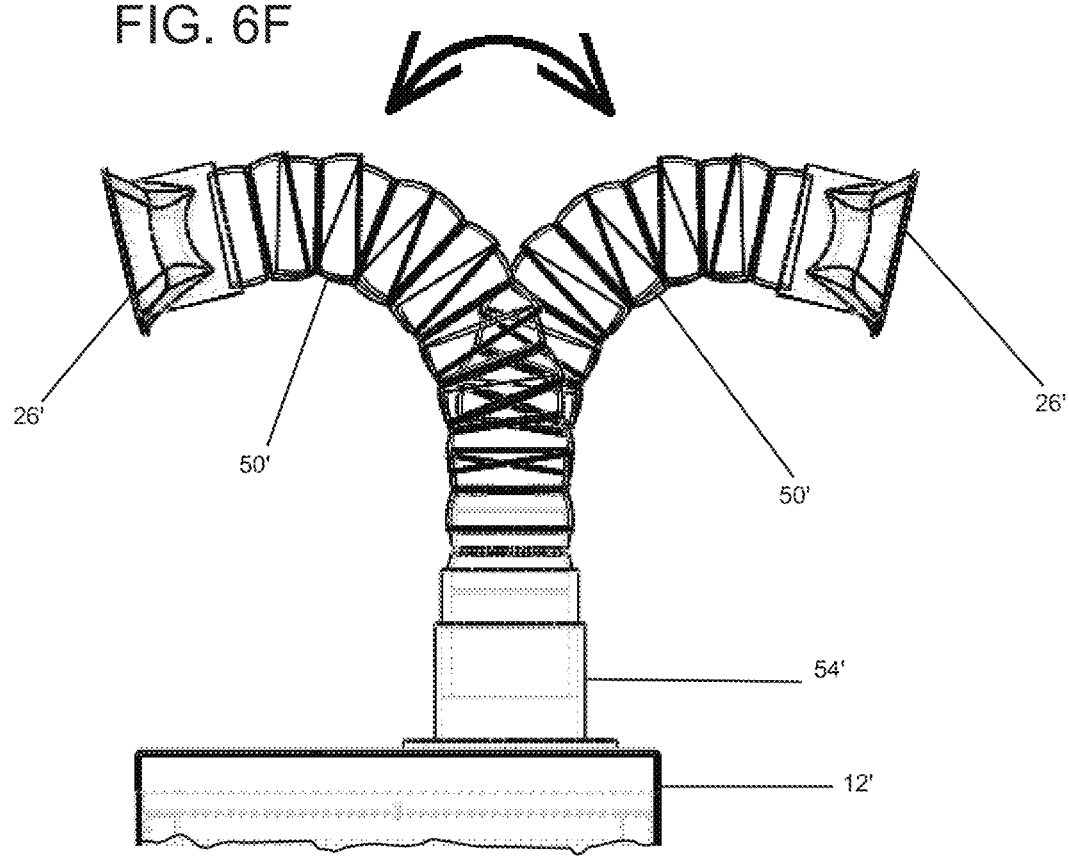

MEDICAL AIR TREATMENT DEVICE

CROSS-REFERENCE TO RELATED APPLICATION

The present application is a continuation of U.S. application Ser. No. 15/813,548 filed Nov. 15, 2017, now U.S. Pat. No. 10,702,435 B2, which claims priority to provisional U.S. Application Ser. No. 62/422,810 filed Nov. 16, 2016, to which Applicant claims the benefit of the earlier filing date. These applications are incorporated herein by reference and made a part hereof.

BACKGROUND OF THE INVENTION

1. Field of the Invention

This invention relates to an air treatment device and, more particularly, an air treatment device having a flexible duct, hose or gooseneck adapted to permit a nozzle end to be situated in proximity to a patient.

2. Description of the Related Art

Health care settings are common grounds for the proliferation of airborne bacteria, viruses and fungi. These agents contribute greatly to hospital acquired infections which drive great human and financial costs to the health care system. A specific concern is the introduction of airborne pathogens arising from certain medical procedures. Pulmonary and airway procedures such as bronchoscopy, laryngoscopy and airway intubation can generate significant airborne pathogens, particularly if the patient is already infected with transmissible agents such as tuberculosis or influenza. These pathogens can generate significant risk to both health care professionals and other patients. Furthermore, the emergence of drug resistant organisms make treatment of hospital acquired infections more difficult. Therefore, there is increased interest in developing environmental solutions which can reduce airborne bioburden and risk of transmissibility.

The typical method for preventing spread of unwanted pathogens arising from a pulmonary procedure is to perform the procedure in a negative pressure room. In a negative pressure room, exhaust air exceeds supply forcing airborne pathogens into exhaust vents rather than into adjacent spaces. Negative pressure rooms, however, present significant problems. First, these rooms have significant engineering requirements, and a typical hospital has a limited supply of such rooms. The volume of procedures can outnumber the negative pressure facilities available. Often it is impractical to transfer patients into negative pressure rooms in order to perform a procedure. Patients may be critically ill, and transfer is risky. Finally, negative pressure rooms do not offer protection for the medical personnel inside of the room. Due to these limitations, hospitals are performing these procedures in normal-pressure patient rooms, intensive care units, and operating rooms.

SUMMARY OF THE INVENTION

What is therefore needed is a device which can create a localized negative pressure zone around a patient within a normal pressure room. This will have the benefit of allowing the use of regular patient rooms as procedure rooms without requiring patient transportation. It will also offer a degree of exposure reduction to personnel within the room, as pathogens will directly enter the device and not the ambient room air. In order for such a device to work, it will need to be capable of creating a vacuum near the patient, have a filtration system to trap air contaminants and an irradiation system to inactivate bacteria.

The features of the embodiments described herein may be used alone or in combination with the features of the embodiments shown and described in U.S. Pat. Nos. 9,433,693; 9,457,119; 9,764,054 and U.S. Patent Publication Nos. 2016/0263267 and 2017/0296691, all of which are incorporated herein by reference and made a part hereof.

One object of the embodiments being described is to provide an air treatment device for treating the air around a patient in a room, such as a surgical room or hospital room.

Another object of the embodiments being described is to provide a flexible and adjustable duct or gooseneck that is adapted and configured to permit a nozzle end to be situated in proximity to the patient.

Still another object of the embodiments being described is to provide an air treatment device that is adapted to create a negative pressure around a patient in order to vacuum the air around the patient into the air treatment system where it can be treated.

Still another object of the embodiments being described is to provide an air treatment system that is adapted to force air past an irradiator for irradiating the airstream entering in the device.

Yet another object of the embodiments being described is to provide an air treatment system that is adapted to reduce or eliminate unwanted airborne bacteria, viruses and fungi.

Yet another object of the embodiments being described is to provide an air treatment device that is portable and that has an inlet end that can be situated in proximity to a patient.

Still another object of the embodiments being described is to provide a system and method for treating air and that may comprise a chemical biocidal remover for reducing or eliminating unwanted pathogens in the airstream.

Yet another object of the embodiments being described is to provide a means for reducing airflow velocity at the irradiator and increasing a time which the airflow is subjected to irradiation by providing at least one or a plurality of airflow interrupters.

Another object of the embodiments being described is to provide a system and method that uses the plurality of airflow interrupters in the form of a plurality of discrete, randomly oriented and radiation-transmitting tubular objects.

In one aspect, one embodiment of the invention comprises an air treatment system for use during a surgical procedure in a room, the air treatment system comprising a housing having an inlet and an outlet, an air treatment device located in the housing for at least one of filtering an airflow or irradiating the airflow before it exits the outlet, and an air hose or duct adapted to be mounted to the housing in communication with the inlet, the air hose or duct having an inlet end for situating in proximity to a patient situated in the room, and an airflow generator for mounting in the housing for generating an air stream between the inlet and the outlet and for creating a negative pressure or vacuum in the air hose or duct, the airflow generator generating an airflow through the air hose or duct to create a negative pressure around a patient during the surgical procedure.

In another aspect, another embodiment of the invention comprises a mobile air treatment device for use with a patient undergoing a procedure, the mobile air treatment device comprising a cabinet that comprises wheels and is portable, a nozzle that is adapted to be positioned in proximity to the patient, means for creating a vacuum or negative pressure at the nozzle, and an air treatment device located in the cabinet for at least one of filtering an airflow or irradiating the airflow before it exits the cabinet.

In yet another aspect, another embodiment of the invention comprises an air treatment device which comprises a flexible air hose with an open nozzle at one end comprising an air inlet, a means for generating a vacuum within the air hose, a filtration means for filtering an air stream emerging from the air hose, a means for the chemical or radiation based inactivation of airborne microbes within the air stream, and at least one of an air outlet adapted for re-entry of treated air into a surrounding space and/or an air outlet adapted for mounting an air duct.

In another aspect, another embodiment of the invention comprises a mobile cabinet comprising a mounting for an air hose, a vacuum generating means, an inactivation means, an air outlet, an air treatment device wherein a nozzle is removable and disposable, the nozzle being of a larger external diameter than the air hose, wherein the nozzle contains an air filtration element, wherein the air hose is semi-rigid and can be re-positioned, wherein the vacuum generating means is a centrifugal blower, wherein the inactivation means comprises an irradiation chamber, wherein the irradiation chamber comprises means for reducing air velocity and linearity, wherein the irradiation chamber comprises a multitude of discrete, randomly oriented, radiation-transmitting objects.

In still another aspect, another embodiment of the invention comprises a method for treating air around a patient comprising placing a nozzle in proximity to a patient, the nozzle connected to an air hose, generating a vacuum in the air hose, creating a localized negative air pressure in the proximity of the nozzle, drawing contaminants arising from the patient and in patient proximity into the nozzle, treating the contaminants by filtration means, treating the contaminants further by biocidal irradiation or chemical means, venting of treated air into the room, or into a duct.

This invention, including all embodiments shown and described herein, could be used alone or together and/or in combination with one or more of the features covered by one or more of the following list of features:

The air treatment system wherein the inlet end comprises a removable nozzle that can be moved or adjusted to a predetermined position by a user.

The air treatment system wherein the nozzle has a nozzle end having a nozzle inlet area that is greater than a cross sectional area of the air hose or duct where the nozzle is coupled to the air hose or duct.

The air treatment system wherein the air hose or duct has at least a portion that is at least one of flexible, pivotable or rotatable.

The air treatment system wherein the nozzle is removable or detachable from the air hose or duct and comprises a filter element.

The air treatment system wherein air treatment device comprises a chemical or irradiator for inactivating airborne microbes within the air stream as the air stream flows between the inlet and the outlet.

The air treatment system wherein the air treatment system is portable.

The air treatment system wherein the air treatment device comprises an air filtration system and at least one of a chemical or irradiating biocidal remover for reducing or eliminating unwanted pathogens in the air stream.

The air treatment system wherein the air treatment device located in the housing filters the air stream and also irradiates the air stream to at least one of filtering the airflow or irradiating the airflow before it exits the outlet.

The air treatment system wherein the air filtration system comprises at least one airflow interrupter for interrupting the air stream to facilitate the at least one of the chemical or irradiating biocidal remover, the at least one airflow interrupter reducing at least one of an air velocity of the air stream or a linearity of a flow of the air stream.

The air treatment system wherein the air filtration system comprises a plurality of airflow interrupters, the plurality of airflow interrupters comprising a plurality of discrete, randomly oriented and radiation-transmitting objects.

The air treatment system wherein the outlet is at least one of adapted to be fitted to a duct in the room or to re-introduce treated air into a surrounding space in the room.

The air treatment system wherein the air treatment system is adapted for use in a room that is not an operating room.

The air treatment system wherein the airflow generator comprises a centrifugal blower.

The air treatment system wherein the air hose or duct is extendable.

The air treatment system wherein the air hose or duct is elongated and semi-rigid with a plurality of areas for permitting a position of the inlet end to be situated in proximity to the patient.

The air treatment system wherein the air hose or duct is an articulating and flexible gooseneck member.

The mobile air treatment device wherein the cabinet comprises an adjustable duct arm having the nozzle removably mounted thereon and coupling the nozzle to the cabinet, the adjustable duct arm being moveable by a user when positioning the nozzle in proximity to the patient.

The mobile air treatment device wherein the cabinet comprises a flexible or semi-rigid hose or duct having an inlet end coupled to the nozzle and an outlet end coupled to the cabinet, the flexible or semi-rigid hose or duct being moveable or adjustable to a predetermined position by a user.

The mobile air treatment device wherein the nozzle has a nozzle end having a nozzle inlet area that is greater than a cross sectional area of the adjustable duct arm where the nozzle is coupled to the adjustable duct arm.

The mobile air treatment device wherein the adjustable duct arm has at least a portion that is flexible or pivotable.

The mobile air treatment device wherein the nozzle is removable or detachable from the adjustable duct arm and comprises a filter element.

The mobile air treatment device wherein air treatment device comprises a chemical or irradiator for inactivating airborne microbes within the airflow as the airflow flows between an inlet and an outlet.

The mobile air treatment device wherein the air treatment device comprises an air filtration system and at least one of a chemical or irradiating biocidal remover for reducing or eliminating unwanted pathogens in the airflow.

The mobile air treatment device wherein the air treatment device located in the cabinet filters the airflow and also irradiates the airflow to at least one of filtering the airflow or irradiating the airflow before it exits an outlet.

The mobile air treatment device wherein the air treatment device comprises at least one airflow interrupter for interrupting the airflow to facilitate the at least one of the chemical or irradiating biocidal remover, the at least one airflow interrupter reducing at least one of an air velocity of the airflow or a linearity of a flow of the airflow.

The mobile air treatment device wherein the air treatment device comprises a plurality of airflow interrupters, the plurality of airflow interrupters comprising a plurality of discrete, randomly oriented and radiation-transmitting objects.

The mobile air treatment device wherein the cabinet comprises an outlet that is at least one of adapted to be fitted to a duct in a room where the patient is located or to re-introduce treated air into a surrounding space in the room.

The mobile air treatment device in combination with a room that is primarily a patient room and not a surgical operating room.

The mobile air treatment device wherein the cabinet comprises an airflow generator for creating the vacuum or negative pressure.

The air treatment system wherein the adjustable duct arm is extendable.

The air treatment system wherein the adjustable duct arm is elongated and semi-rigid with a plurality of areas for permitting a position of an inlet end to be situated in proximity to the patient.

The air treatment system wherein the adjustable duct arm is an articulating and flexible gooseneck member.

These and other objects and advantages of the invention will be apparent from the following description, the accompanying drawings and the appended claims.

BRIEF DESCRIPTION OF THE ACCOMPANYING DRAWINGS

FIG. 3A is an exploded view of the air treatment system showing the various components of the air treatment system;

FIG. 3B is an enlarged view of the coupling of the elbow and duct member along the line 3B-3B in FIG. 2C;

FIGS. 6A-6F are views of another embodiment showing an adjustable gooseneck and flexible duct.

DETAILED DESCRIPTION OF THE PREFERRED EMBODIMENTS

Figure 1:
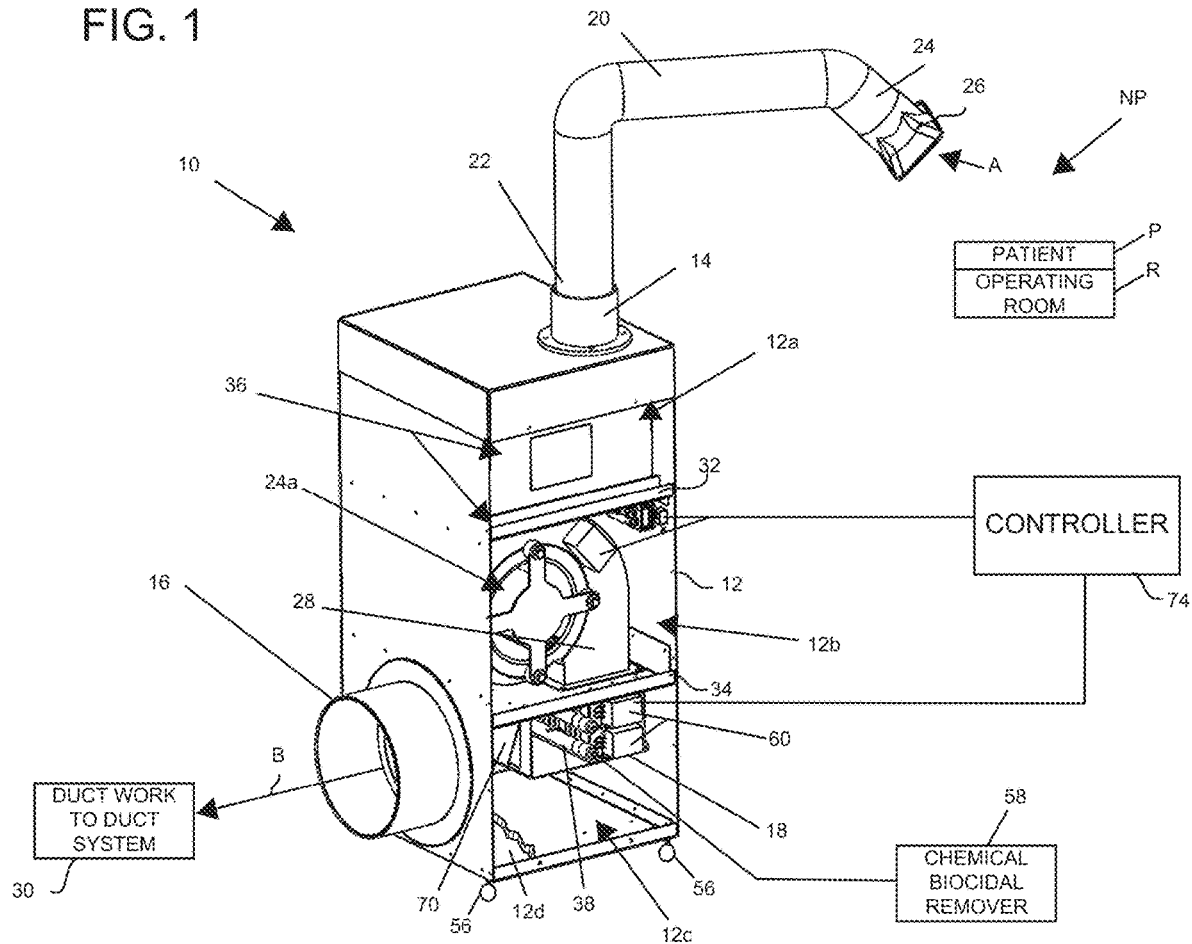
FIG. 1 is a perspective view of an air treatment system in accordance with one embodiment.

Referring now to FIG. 1, an air treatment system 10 is shown. The air treatment system 10 is adapted for use during a surgical procedure in a room, such as an operating room R, where it is desired to treat or purify the air around a patient P.

The air treatment system 10 comprises a housing 12 having an inlet 14 and an outlet 16. The housing 12 has an air treatment device 18 situated and mounted therein. The air treatment device 18 is adapted to filter, treat, sanitize and/or irradiate the air entering the inlet 14 and passing through the air treatment system 10 before exiting the outlet 16.

The air treatment system 10 comprises an air hose or duct 20 adapted to be mounted in communication with the inlet 14. In this regard, the air hose or duct 20 comprises an end 22 that is mounted to and in communication with the inlet 14 as illustrated in FIG. 1. The air hose or duct 20 has an inlet end 24 having a nozzle 26 detachably secured thereto. In the embodiments being described, the air hose or duct 20 is adjustable and has a flexible gooseneck member having an adjustable and flexible gooseneck whose position can be changed and adjusted to permit positioning the nozzle 26 in proximity to a patient P. Features of another adjustable gooseneck are also illustrated in another embodiment shown in FIGS. 6A-6F. The air hose or duct 20 is at least one of flexible, pivotable, rotatable or extendable (i.e., telescopic) so that the nozzle 26 may be situated in proximity to the patient P (FIG. 1) situated in the room R.

The air treatment system 10 further comprises an airflow generator 28. In the illustration being described, the airflow generator 28 is conventionally mounted in the housing 12 and generates an airstream between the inlet 14 and the outlet 16, which in turn, creates a negative pressure or vacuum in the air hose or duct 20 and particularly at the area A associated with the inlet end 24 and nozzle 26. In general, this negative air pressure at the area A causes the air around the patient P to be pulled or sucked into nozzle 26, into the air hose or duct 20, and then into the housing 12 where the air flows through the housing 12 and is treated by the air treatment system 10.

Figure 2A:
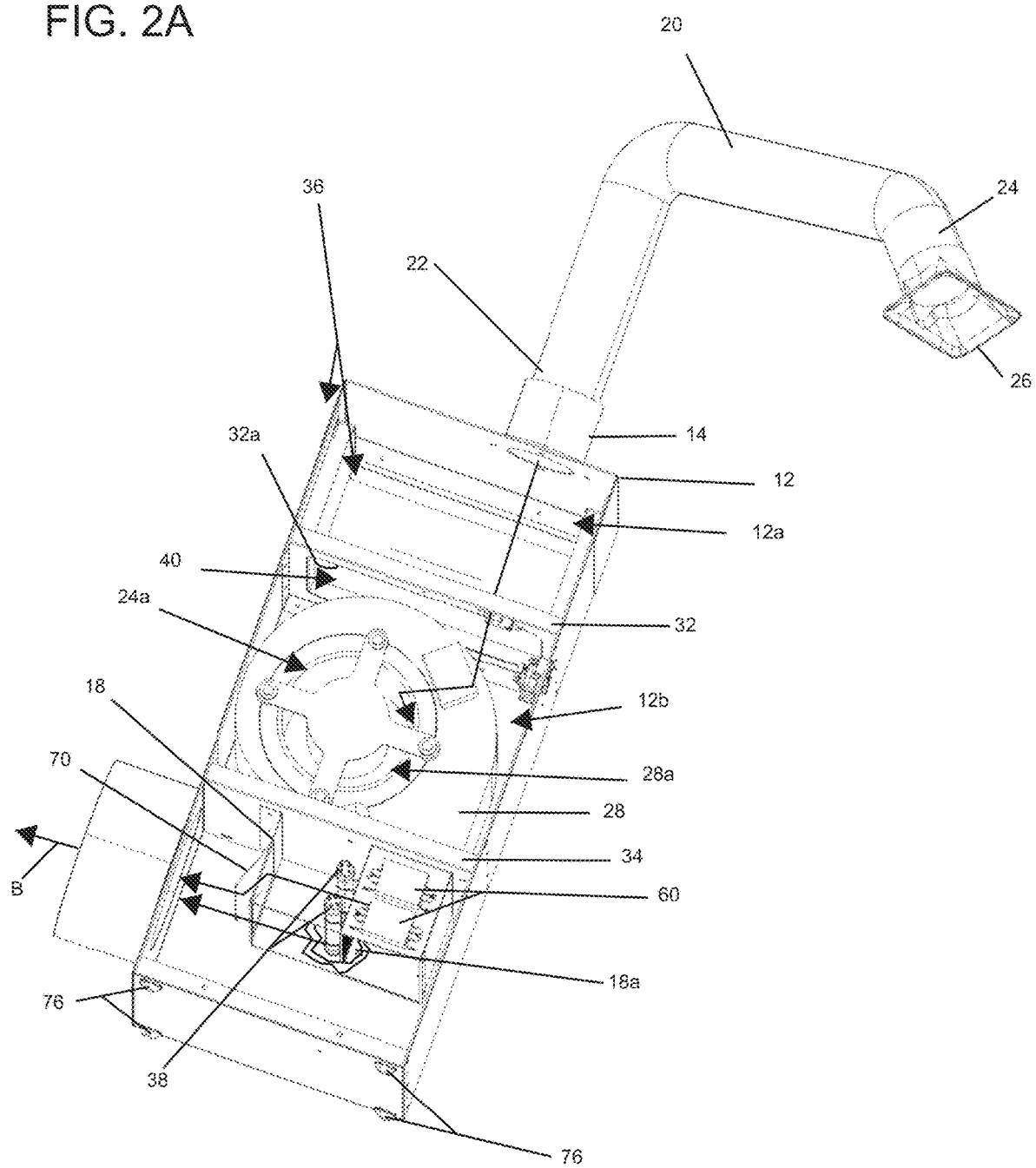
FIGS. 2A-2C are additional views of the embodiment shown in FIG. 1 illustrating the movement of a duct or hose.

Notice in FIGS. 1 and 2A that the housing 12 comprises a first chamber area 12a, a second chamber area 12b wherein the airflow generator 28 is situated, and an air treatment area or chamber 12c wherein the airflow passing through the housing 12 is treated before it exits in the direction of arrow B (FIGS. 1, 2A and 2C) through the outlet 16. In the illustration being described, the outlet 16 may be open to atmosphere in the operating room R or it may be coupled to conventional duct work, including flexible duct work (not shown), where the air would be exhausted through a duct system 30 as illustrated in FIG. 1.

In the illustration being described, the housing 12 comprises a plurality of housing dividers or supports 32 and 34 which are in an internal chamber 36 (FIG. 2A) of the housing 12 and which receives air from the air hose or duct 20. A wall 32a in support 32 defines a passageway 40 that allows the air to pass from chamber 12a into the chamber 12b wherein the airflow generator 28 is situated. The airflow generator 28, when activated, causes air in the chamber 12b to be sucked or pulled into the airflow generator housing 28a so that the airflow generator 28 can cause the air to flow from the first chamber area 12a and into the second chamber area 12b to be exhausted from the second chamber area 12b into the third chamber area 12c where it is treated by the air treatment device 18. In this regard, the airflow divider or support 34 comprises at least one generally rectangular opening 39 (FIG. 2B) so that the airflow generator 28 forces air to pass into the third chamber area 12c and past the components of the air treatment device 18.

The air treatment device 18 comprises at least one or a plurality of irradiators 38 which irradiate the airstream and kill unwanted bacteria, viruses and/or fungi. In the illustration being described, the at least one or a plurality of irradiators 38 comprise at least one or a plurality of ultra-violet light sources for providing the irradiation in the manner conventionally known. Although not shown, one or more features of the devices and apparatus shown in the U.S. Pat. Nos. 9,433,693; 9,457,119; 9,764,054 and U.S. Patent Publication Nos. 2016/0263267 and 2017/0296691, all of which are assigned to the same Assignee as the present application, may be used in conjunction with or as the air treatment device 18. These U.S. Patents and published U.S. patent applications are incorporated herein by reference and made a part hereof. For example, U.S. Pat. No. 9,457,119 shows a generally rectangular box holding a plurality of quartz tubular members. It is contemplated that features of this device may be used with or in combination with the irradiator 38.

Figure 2B:
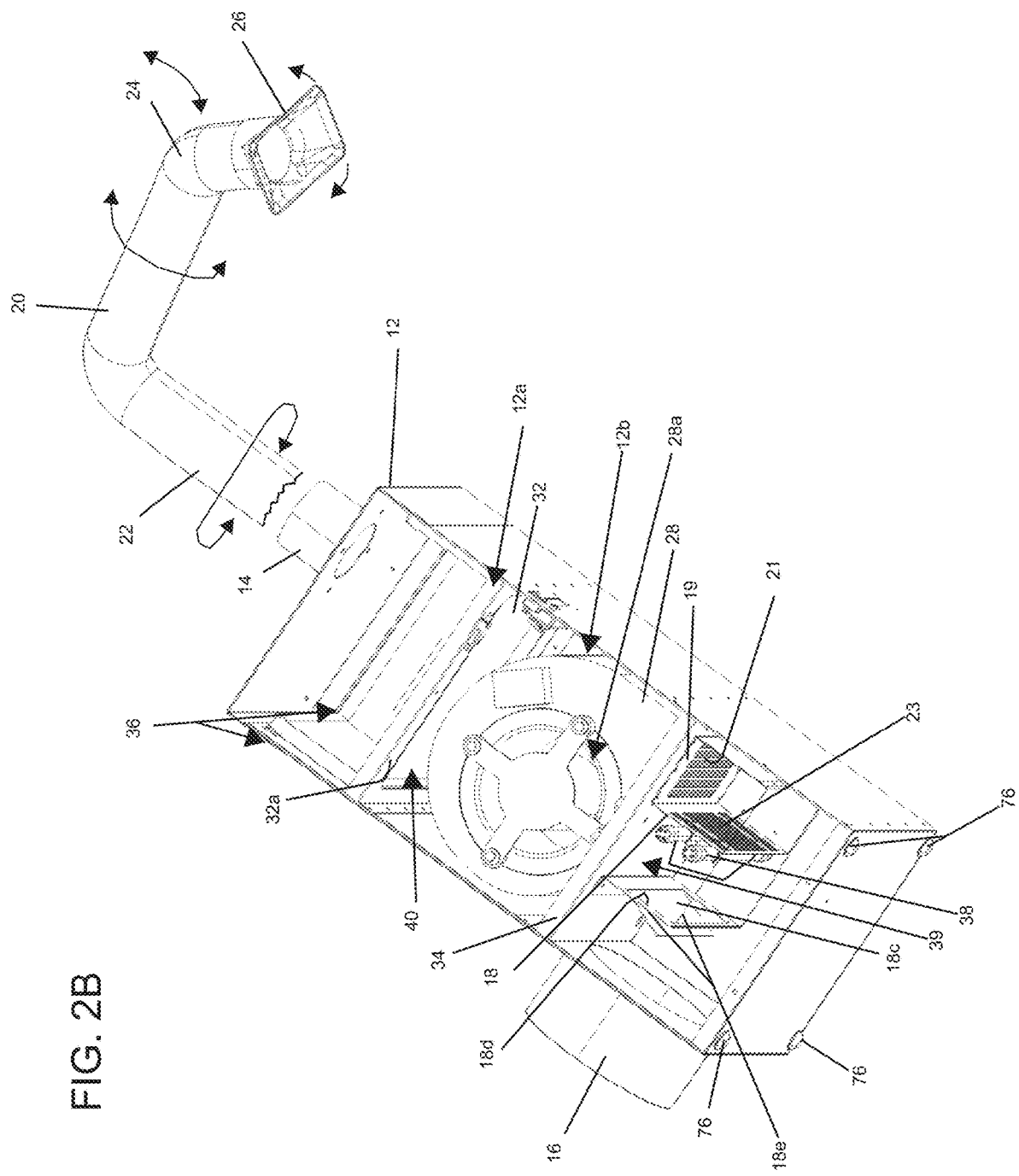
Figure 2C:
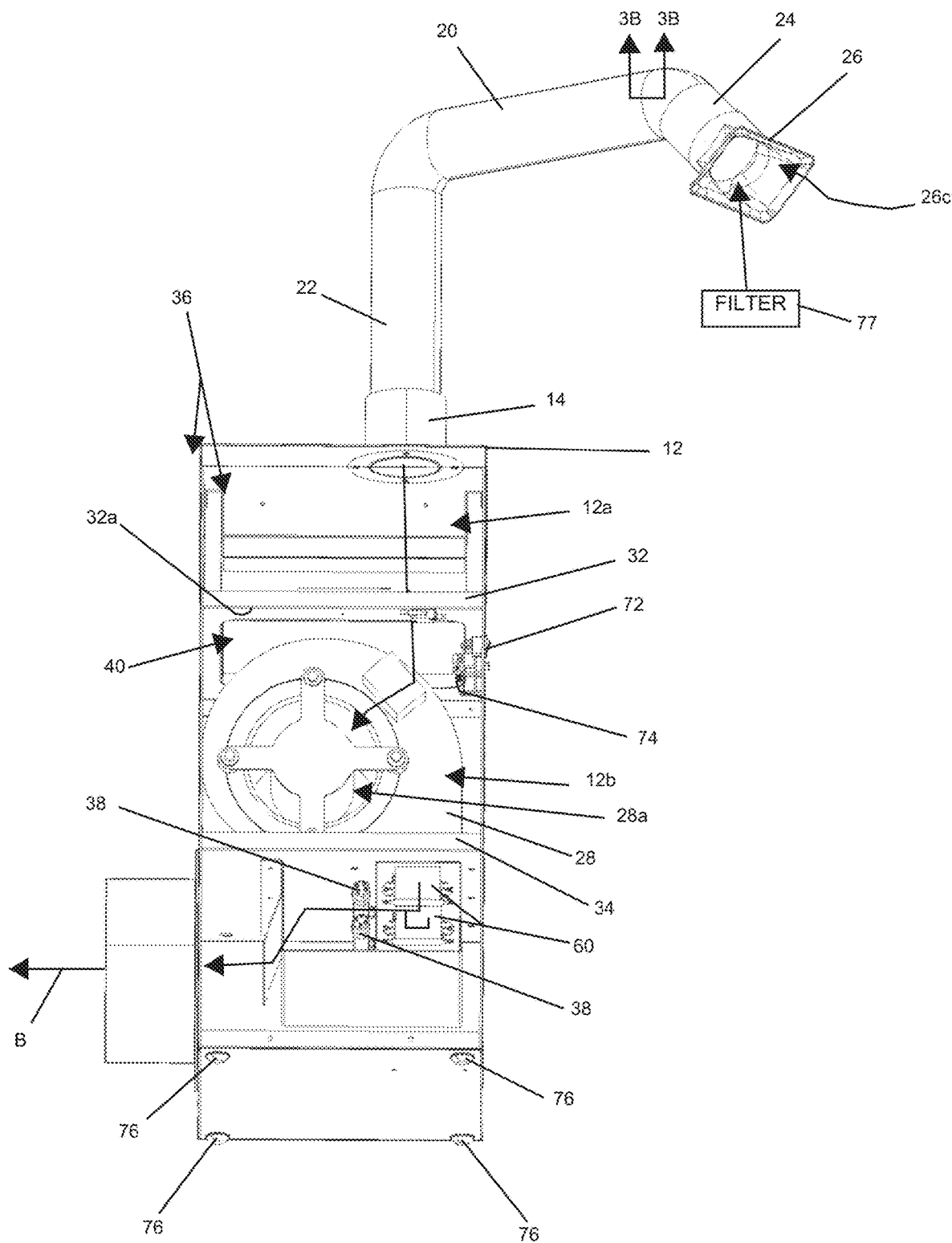

It is also contemplated that the air treatment device 18 may comprise a chemical treatment or biocidal remover 58 (FIG. 1) for inactivating or destroying airborne microbes within the air stream as the air stream flows between the inlet 14 and the outlet 16 of the air treatment system 10. It should be understood that the housing 12 of the air treatment system 10 comprises a front panel 13 (FIGS. 6B and 6D), and a side panel 15 (FIG. 6D) which is shown removed in FIGS. 1, 2A-2C and 5F-5G in order to illustrate the components therein. With the panel removed, it can be seen that the air flows into the air hose or duct 20 and into the inlet 14 of the housing 12 where it reaches the first chamber 12a. The airflow passes through the opening or passageway 40 (FIG. 2A) defined by a wall 32a of the divider or support 32 and into the second chamber 12b as illustrated in FIG. 2A. The air flows into the airflow generator 28, which in the illustration being described is a centrifugal fan, which receives air in the area 28a and directs the air through the fan housing 24a where it is directed into the air treatment device 18. As illustrated in FIG. 2, the air is caused to be directed through the air treatment device 18 and past the irradiators 38. In this regard, the air treatment device 18 comprises a generally L-shaped grate 19 (FIG. 2B) that comprises a plurality of inlet vents 21 and outlet vents or grates 23, with the outlet vents or grate 23 being associated with the at least one or a plurality of irradiators 38. The air is directed past the at least one or a plurality of irradiators 38 and through an exit aperture 18c (FIG. 2B) defined by a wall 18d in the air treatment device housing 18a. Although not shown, it should be appreciated that the air treatment device 18 is closed on its sides by either a separate wall that is mounted on the edges 18e or that is closed and sealed by the front cover 12d so that all air that enters into the air treatment device 18 flows through the outlet vents or grates 23 and past the irradiators 38 as illustrated in FIG. 2B. This causes all airflow entering into the housing 12 to be received and pass through the air treatment device 18 so that the air can be purified in order to reduce or eliminate airborne bacteria, viruses and fungi in the airstream and before it is passed through the outlet 16.

In the illustration, a controller 74 (FIG. 1) is coupled to and controls the various components (i.e., the airflow generator 28 and the air treatment device 18). When the switch 72 (FIG. 2C) is activated, the airflow generator 28 and air treatment device 18 are energized to cause the air treatment system 10 to treat the air around the patient P.

Referring now to the exploded view in FIG. 3A, details of the air hose or duct 20 of the first embodiment are shown. In one embodiment, the duct 20 comprises mating segments 20a-20e. Note that the elbows 20b and 20d each have an internal wall 20b1 and 20d1, respectively that define a plurality of female apertures adapted to receive male ends of the mating segments or members 20a, 20c and 20e. For example, the duct member 20c comprises the first male end 20c1 and the second male end 20c2 that are received in the elbows 20b and 20d, respectively, as shown. Note that the segment 20a also comprises a male portion 20a1 that is adapted and sized to be received in the female aperture of the elbow 20b. The segment 20a further comprises the inlet 14 to thereby secure the air hose and duct 20 to the housing 12. The segment 20e also comprises male ends 20e1 and 20e2. The end 20e1 is adapted and sized to be received in the elbow 20d. The end 20e2 is adapted and sized to receive the nozzle 26 as shown.

Once the various segments 20a-20e and the nozzle 26 are assembled and the segment 20a is mounted on the inlet 14, the nozzle 26 can be situated and moved in operative relationship with the patient P (FIG. 1) so as to create a negative pressure NP (FIG. 1) around the patient P and in order to cause the air around the patient P to be received, vacuumed, sucked or pulled into the air hose or duct 20 where it can then be received in the housing 12 and processed as described herein. It should be understood that, in a preferred embodiment, the air hose or duct 20 is flexible with each section being pivotable or rotatable so that the nozzle 26 may be moved to a desired position relative to the patient P.

It should be understood that various means may be used to rotatably couple the various components 20a-20e together. For example, FIG. 3B shows an example along the line of 3B-3B in FIG. 2C of a coupling of the elbow 20b and duct member 20c, showing use of a boss 23a and mating circumferencing channel 25 in the duct member 20c. The boss 23a and channel 25 may be continuous or interrupted and facilitate rotatably retaining the joining parts together, while permitting the parts to be pivoted or rotated relative to each other.

As mentioned, the air hose or duct 20 comprises at least a portion that is at least one of flexible, pivotable or rotatable so that a position of the nozzle 26 may be adjusted. The air hose or duct 20 may be made from a flexible material, coating or sheath (not shown) or other flexible material that can be formed into the shape of a tube and that is flexible. Although not shown, an insulation layer or other protective layer, such as polyester, glass, polyethylene or PET can be used on the duct 20. In the illustration being described, the flexible duct 20 is adapted to accommodate negative pressures, such as negative pressure of 200 Pa or more.

Figure 4A:
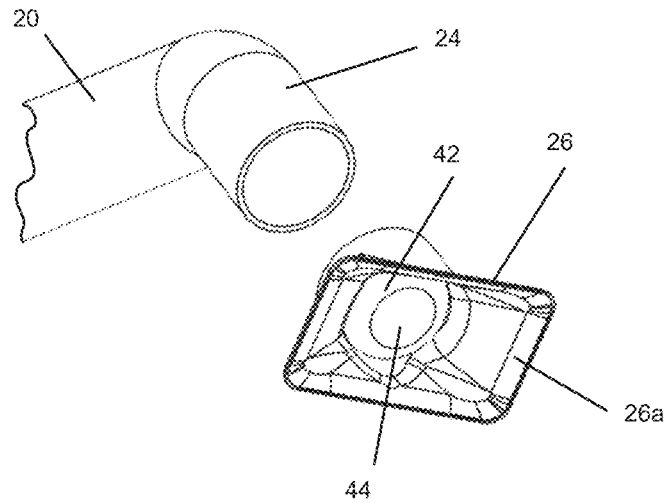
FIGS. 4A-4C are fragmentary views showing various features of the nozzle and a ball valve used therein.
Figure 4B:
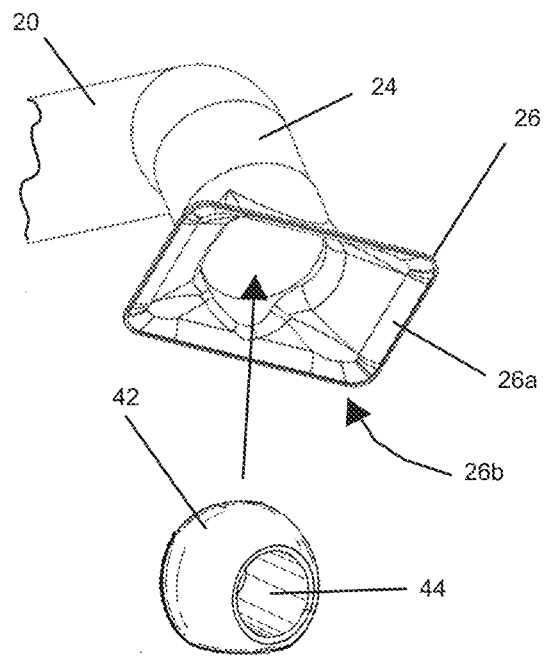
Figure 4C:
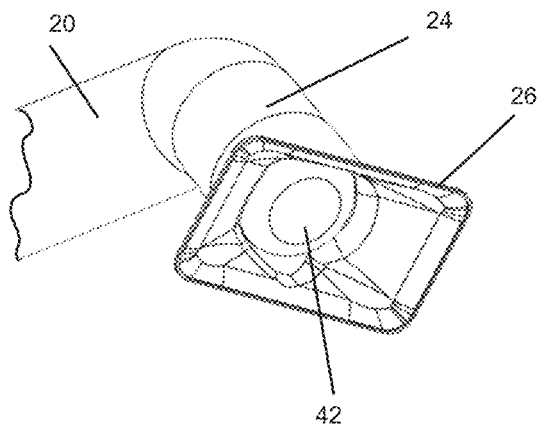
Figure 5A:
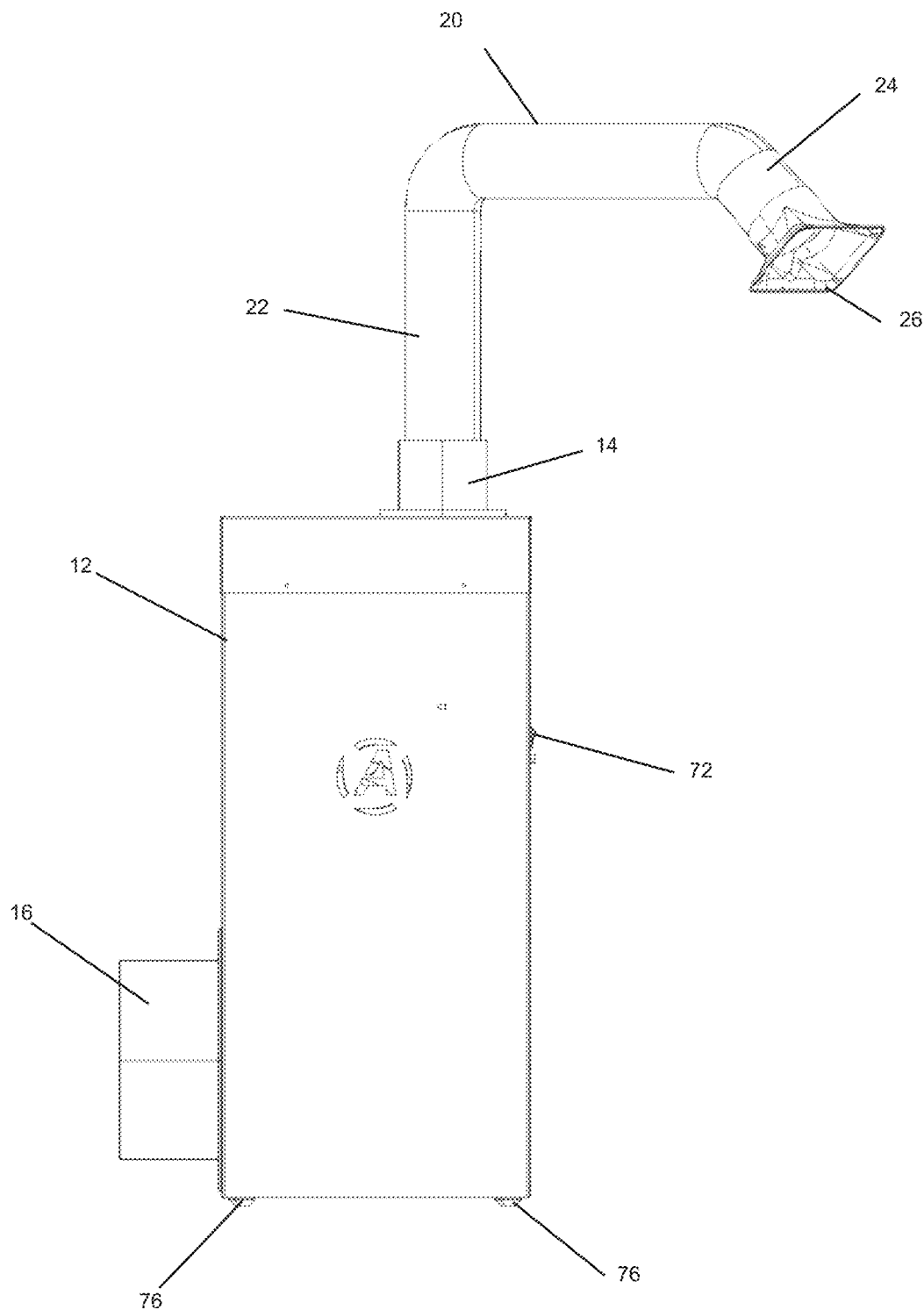
FIGS. 5A-5G are additional views, some with the side cover of a housing of the air treatment system removed, illustrating various features of the embodiment shown.
Figure 5B:
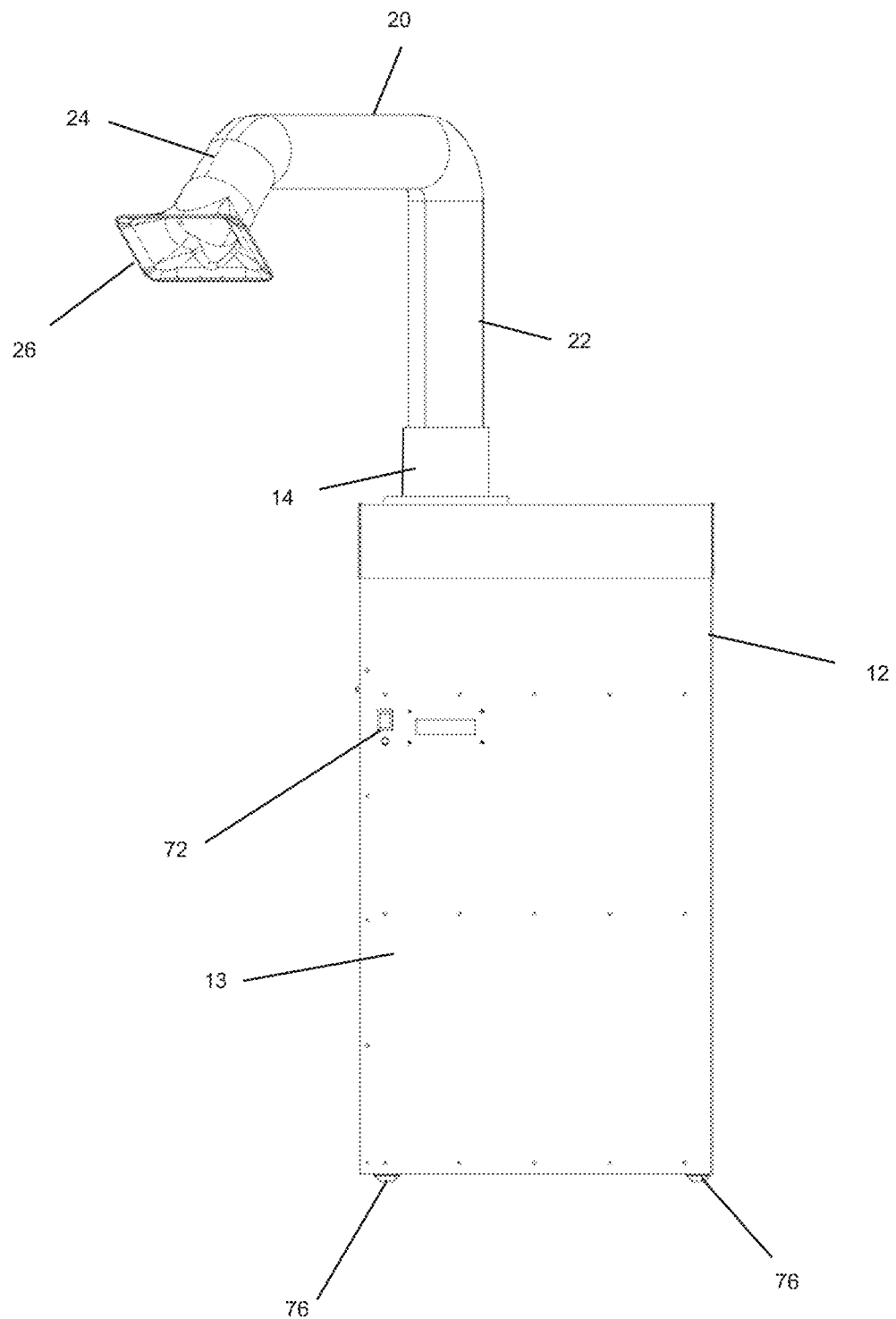
Figure 5C:
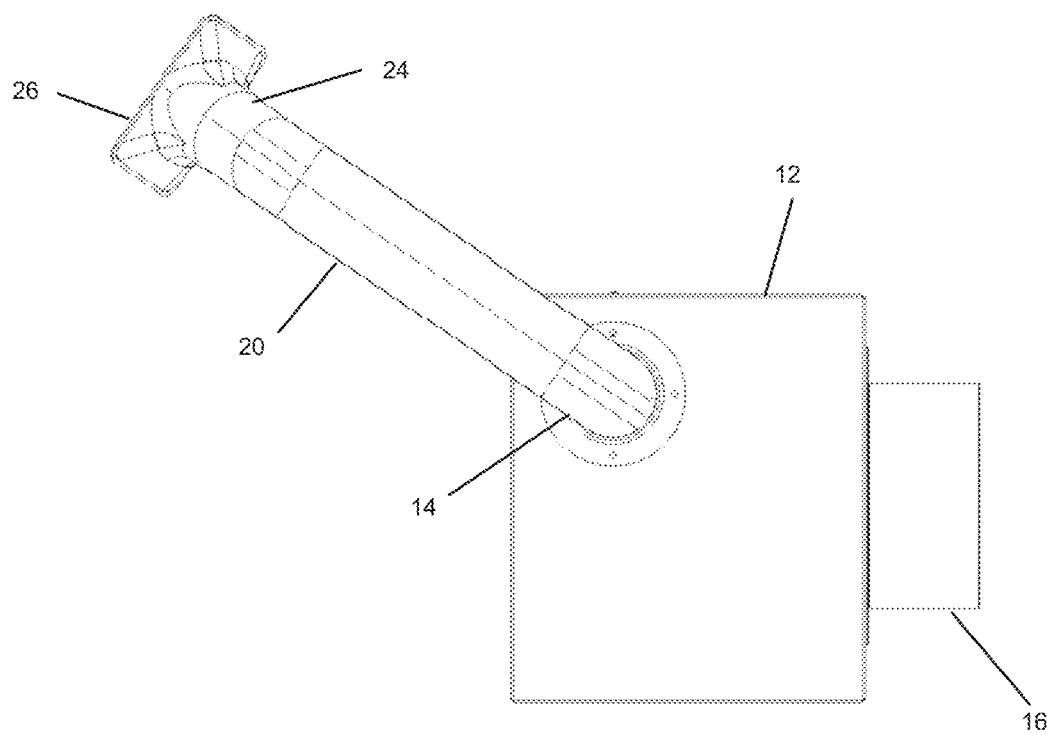
Figure 5D:
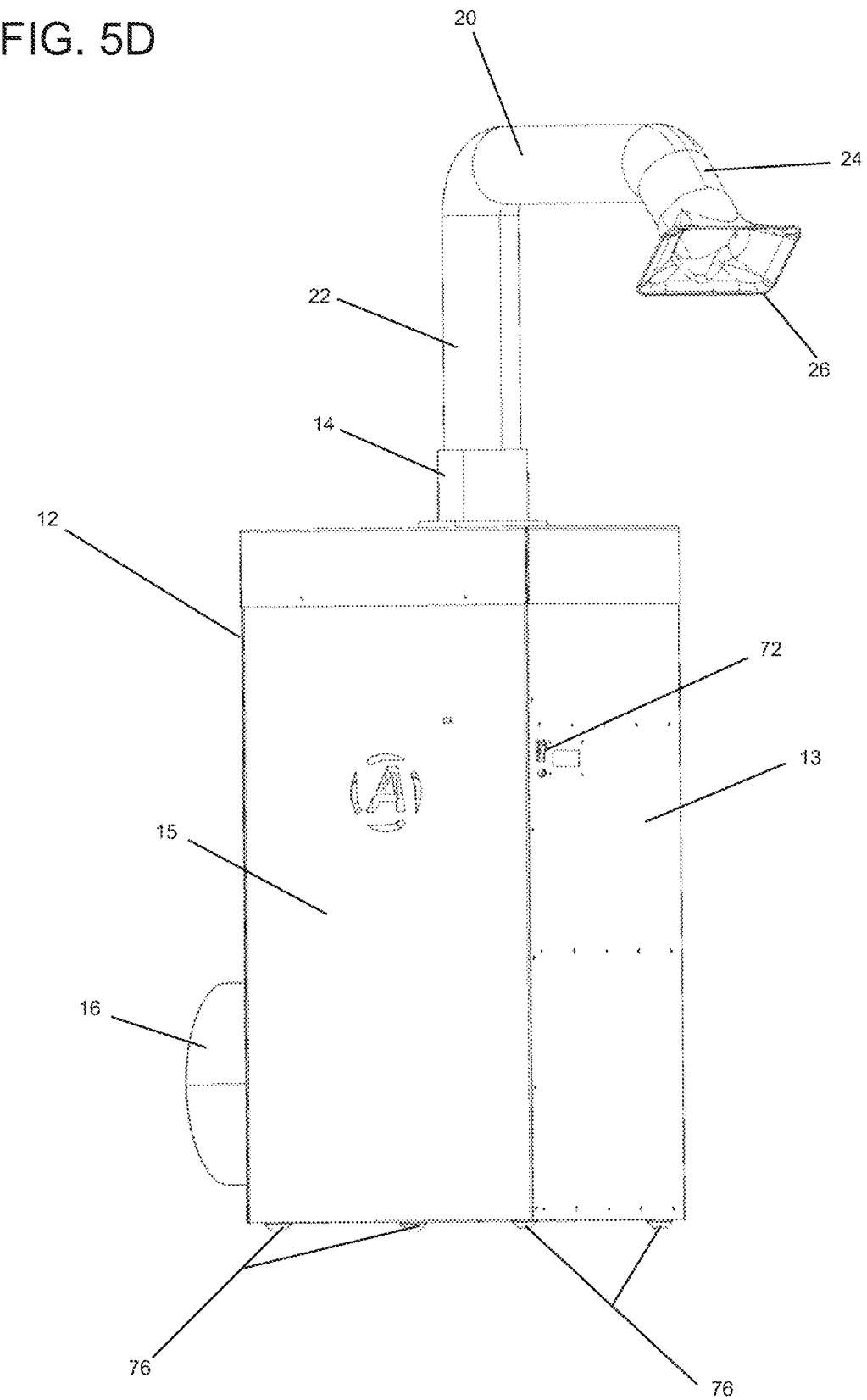
Figure 5E:
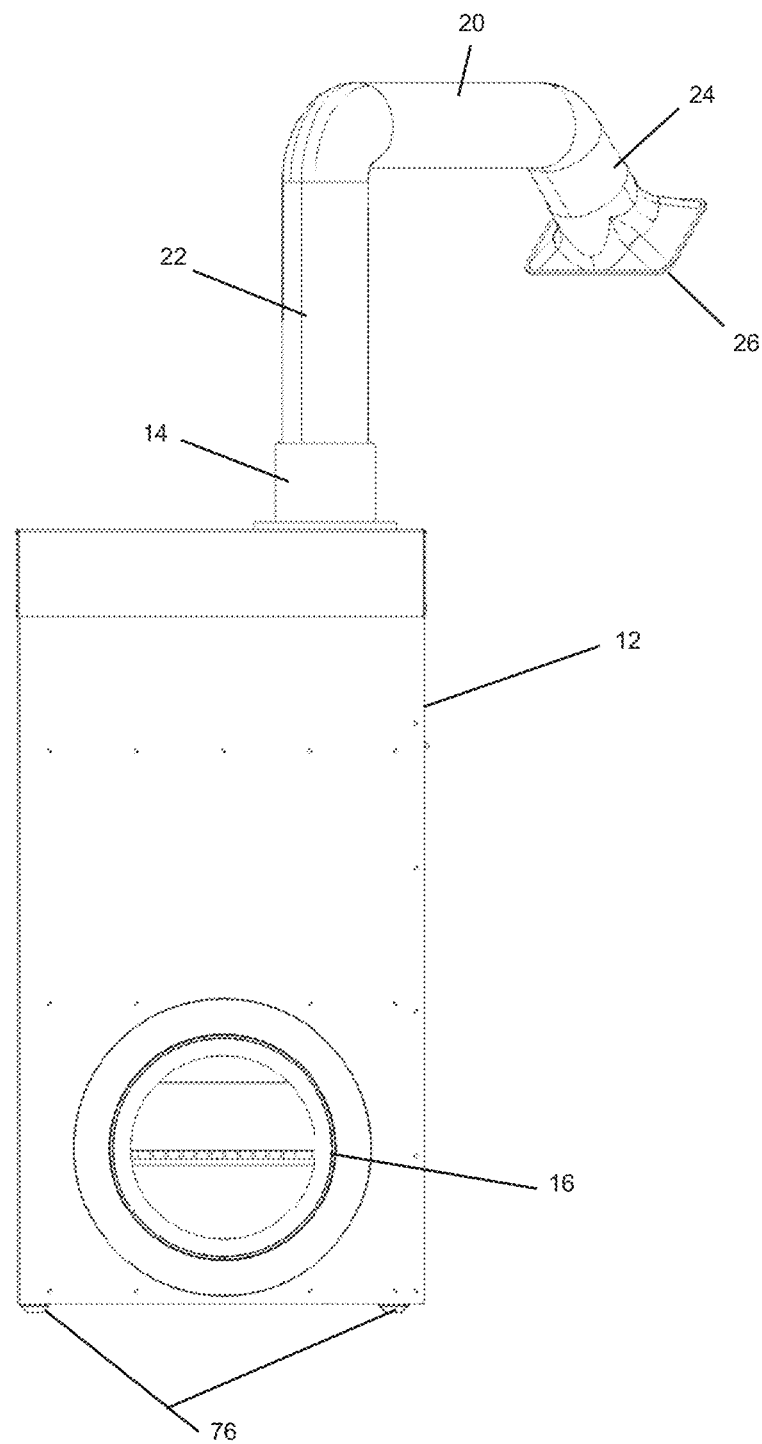
Figure 5F:
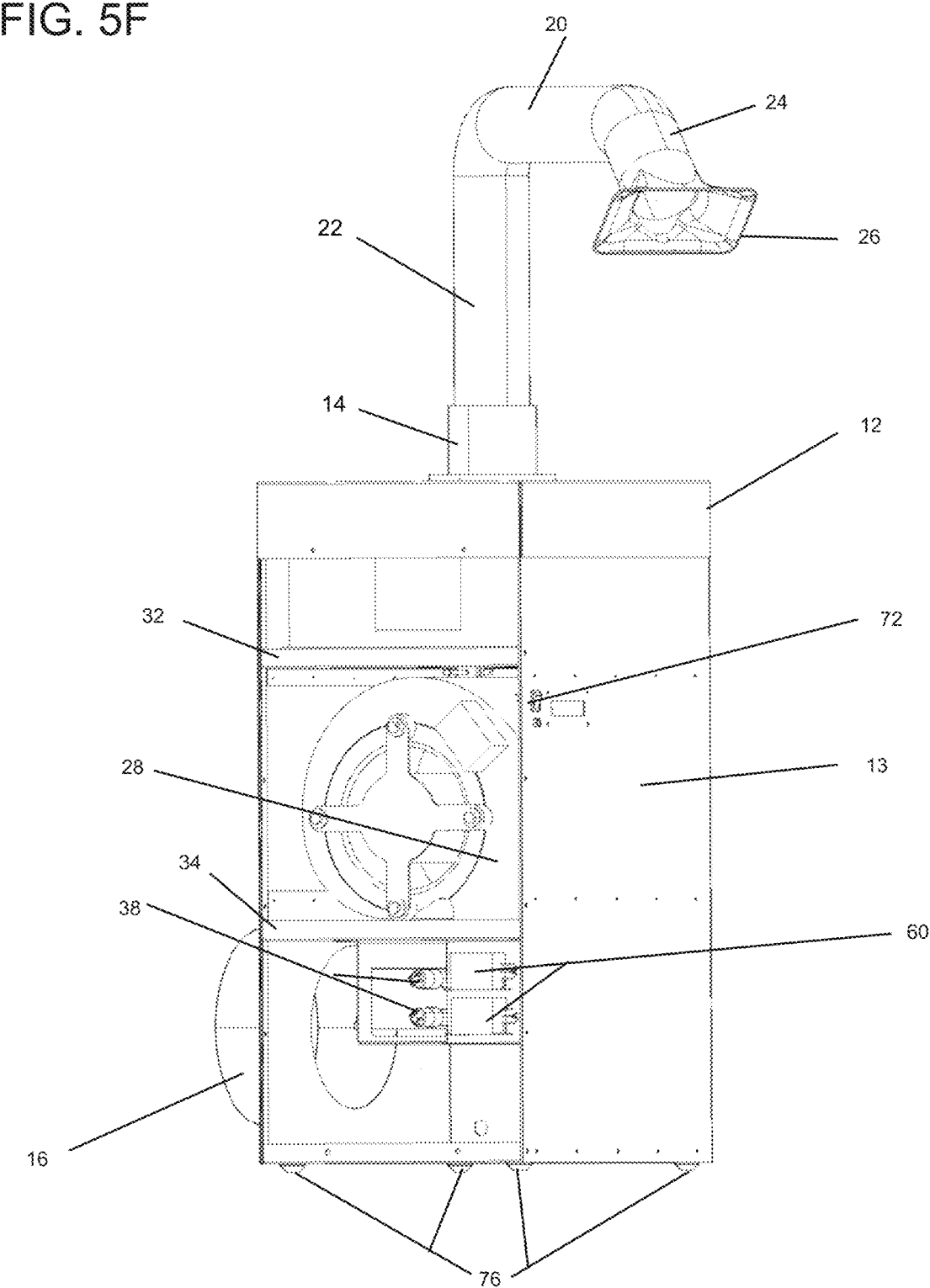
Figure 5G:
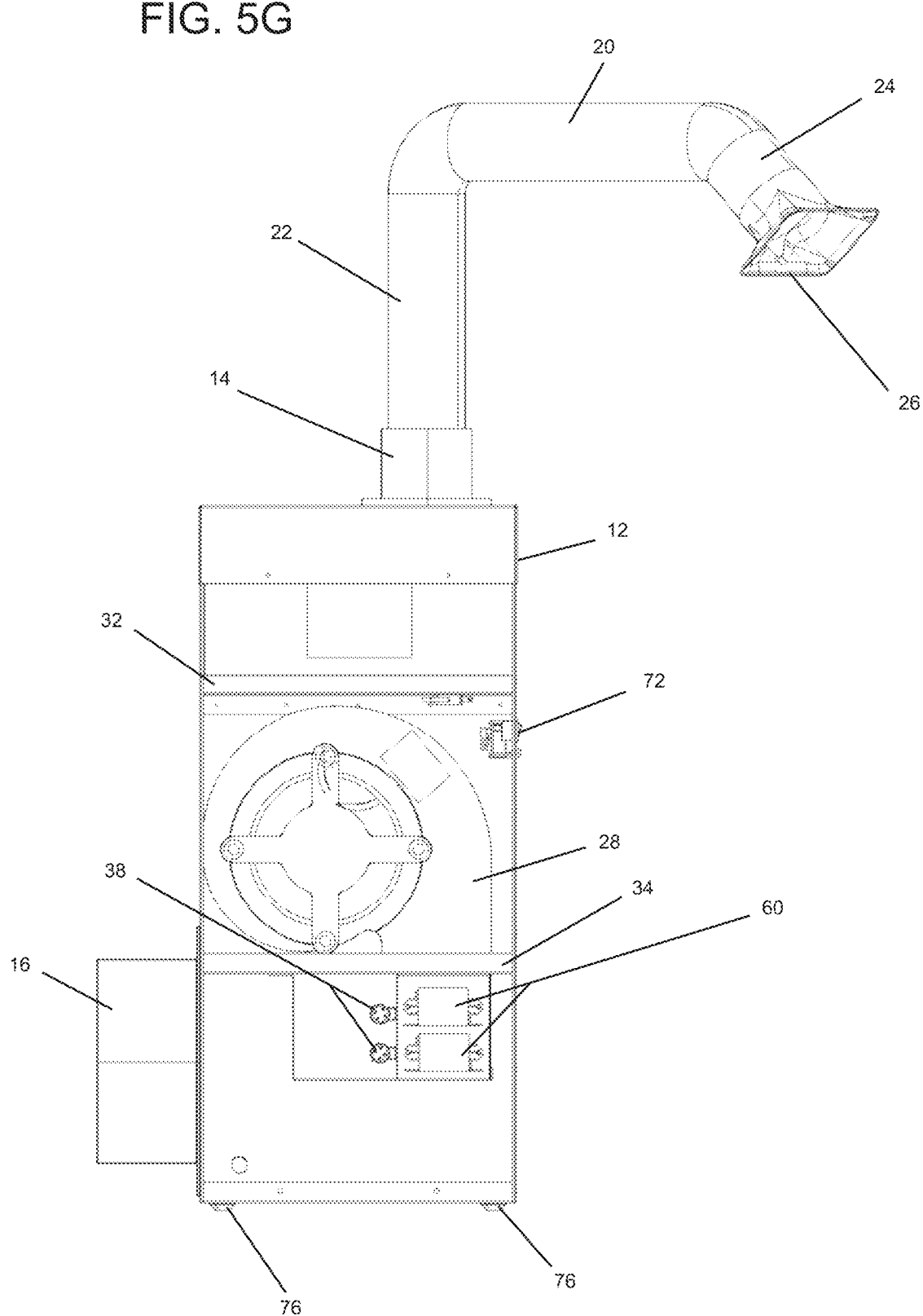

Referring to FIGS. 4A-4C, details of the nozzle 26 are shown. Note that the nozzle 26 has a nozzle end 26a that defines a nozzle inlet area 26b that is greater than a cross-sectional area of the air hose or duct 20 where the nozzle 26 is coupled to the air hose or duct 20. Note that the nozzle 26 may comprise an adjustable ball valve 42 that is generally spherical and has an aperture 44 therethrough. In the illustration being described, the ball valve 42 is press-fit into the nozzle 26 as shown in FIG. 4C.

Figure 6A:
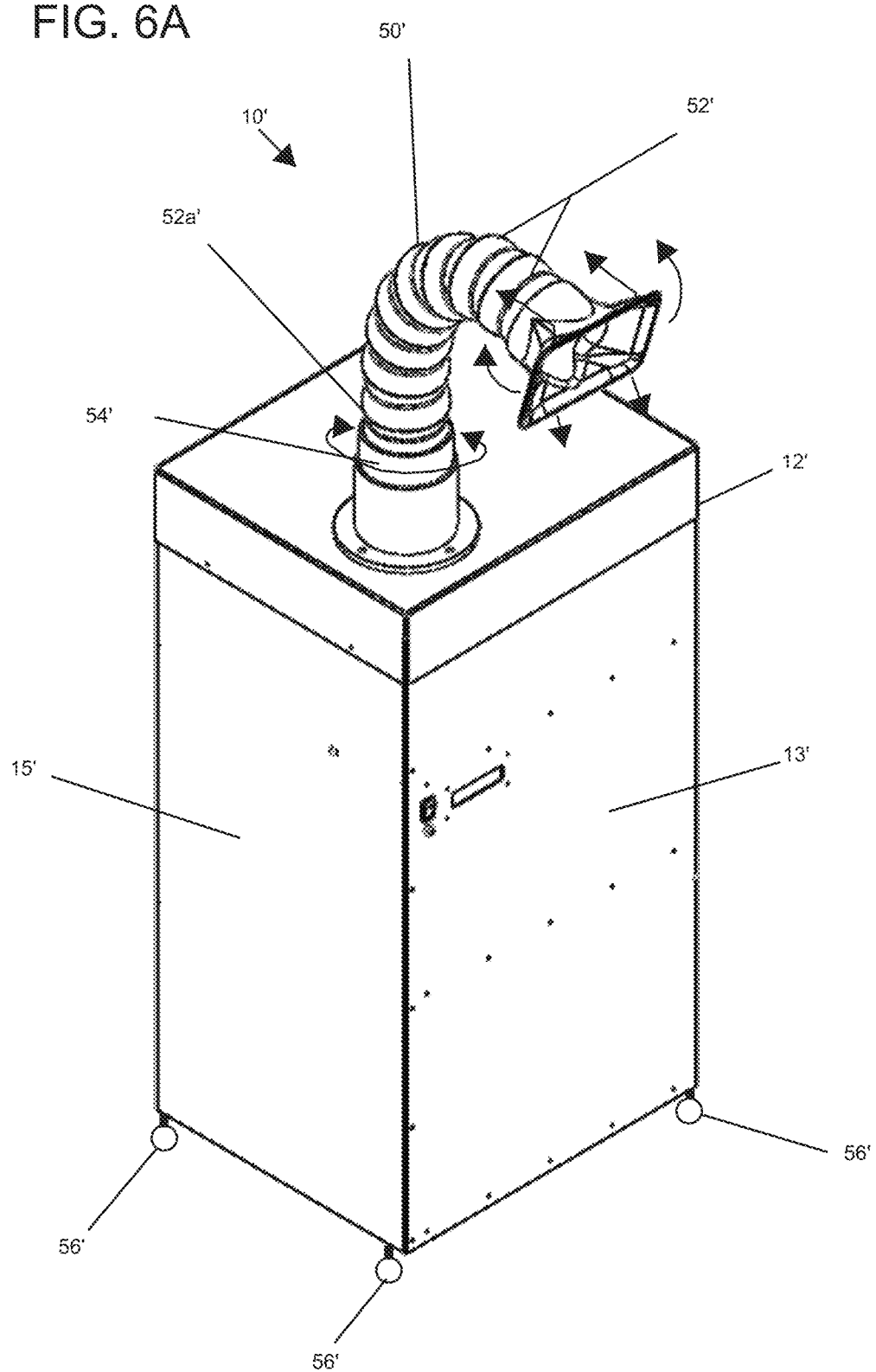
Figure 6B:
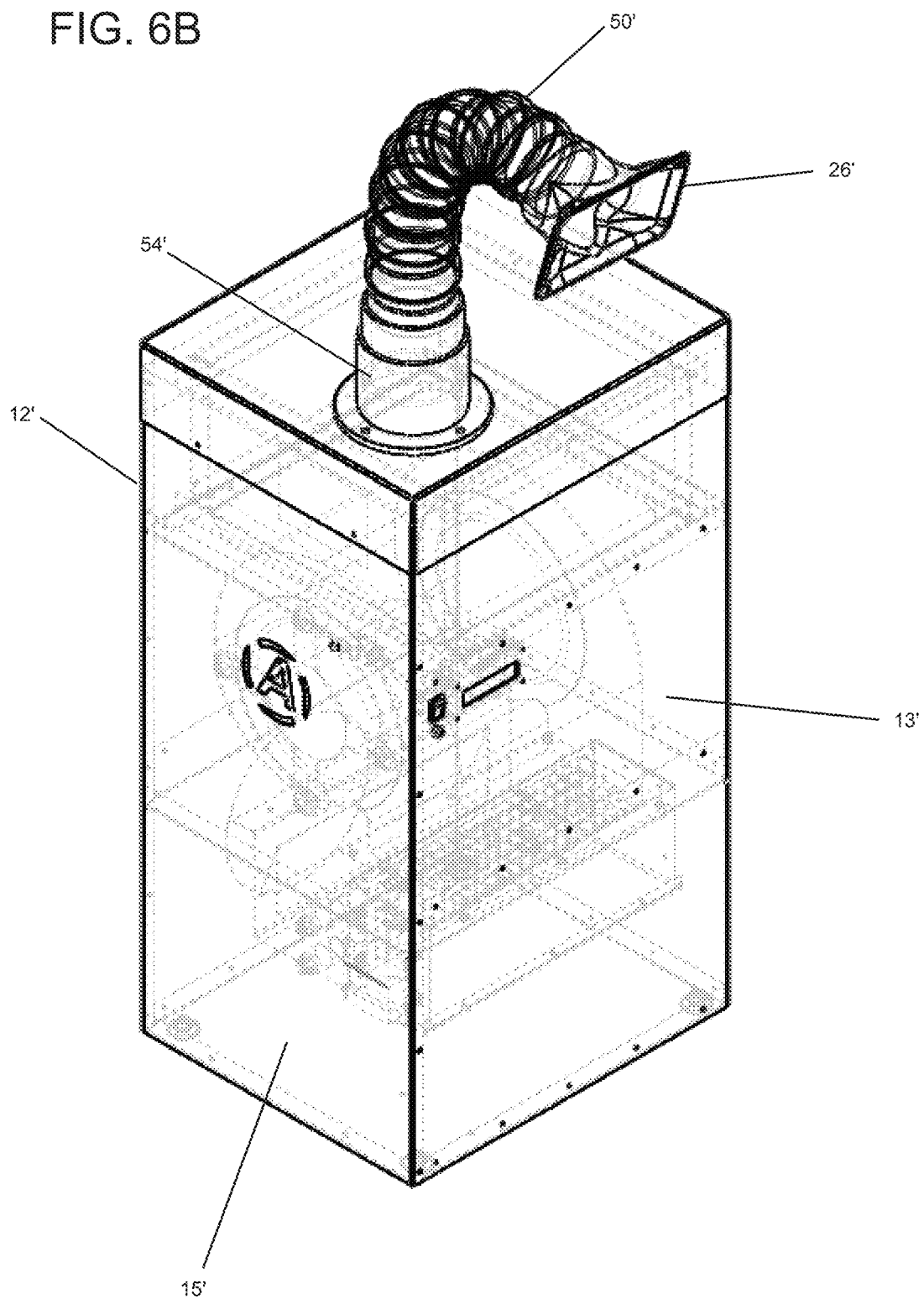
Figure 6C:
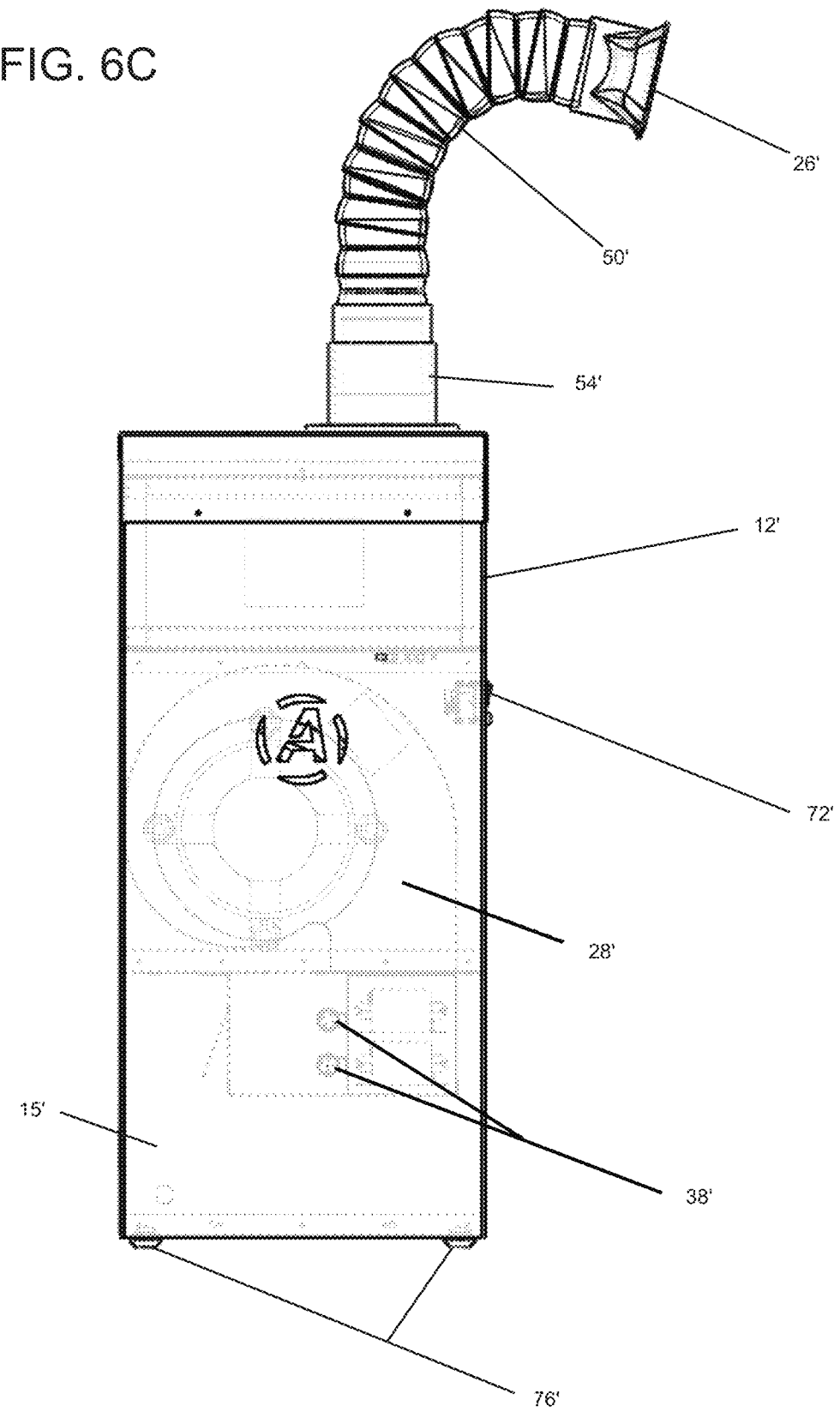
Figure 6D:
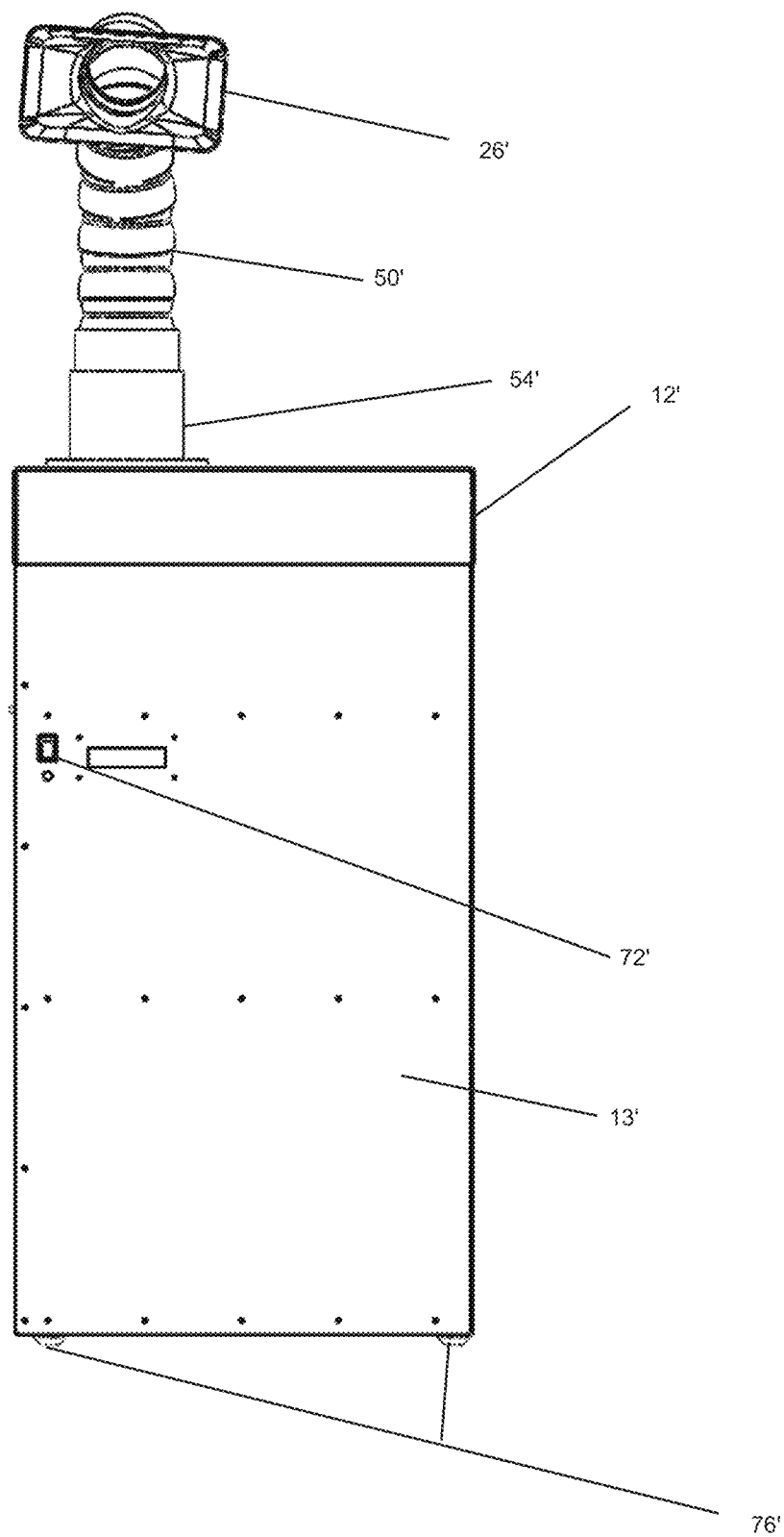
Figure 6E:
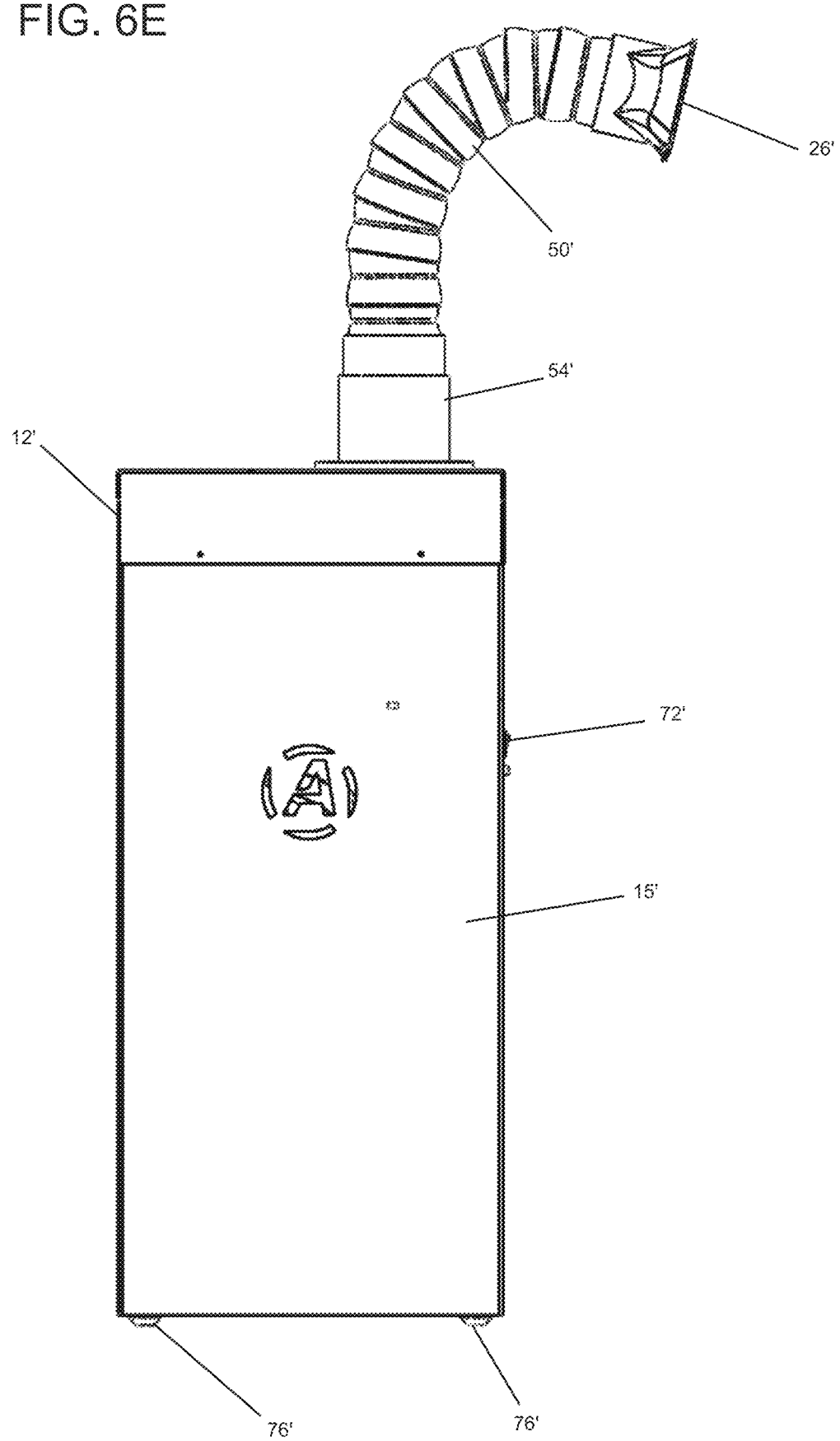

FIG. 6A illustrates the air treatment system 10 comprising a plurality of rubber pads 76 for supporting the housing 12, but as mentioned earlier, it should be appreciated that the housing 12 could comprise the plurality of wheels 56, such as caster wheels, to facilitate ease of portability and movement of the air treatment system 10.

In one embodiment, the air treatment system 10 comprises a plurality of irradiators 38 (FIG. 2A) in the form of ultraviolet lamps that are conventionally coupled to a ballast 60 with end cap connectors and lamp holder (not shown). It should be understood that the air treatment system 10 may comprise a chemical biocidal removal 58 in the chamber 12c in place of or in addition to the plurality of irradiators 38. Also, the air treatment device 18 may comprise at least one airflow interrupter for interrupting the airstream to facilitate causing the airstream to be subjected to the irradiation for a longer period of time thereby facilitating the removal and spread of unwanted pathogens. In this regard, the features of U.S. Pat. No. 9,457,119 (tubular transparent members) may be used herein. Note in the embodiment being described that the air treatment system 10 comprises a baffle 70 (FIG. 1) associated with the chamber 12c. As is conventionally known, the baffle 70 interrupts the linear air flow so that the airflow velocity is reduced and a linearity of the flow of the air stream is interrupted which in turn causes the airstream to be subjected to the irradiation generated by the irradiators 38 or the chemical biocidal remover 58.

Note in FIG. 2C that the air treatment system 10 further comprises the switch 72 coupled to the printed circuit board or controller 74 which controls the operation of the airflow generator 28 and the air treatment device 18.

In general, the user positions the air treatment system 10 in proximity to the patient P and maneuvers the gooseneck air hose or duct 20 such that the nozzle 26 is positioned in proximity to the patient P. The user actuates the switch 72 which in turn causes controller 74 to energize the airflow generator 28 to cause a negative pressure at the nozzle 26 which sucks or vacuums the air into the air treatment system 10 through the chambers 12a, 12b and into the chamber 12c where the airstream experiences the air treatment device 18. In the illustration shown, the air treatment device 18, which is also energized by controller 74 in response to activation of the switch 72, has the irradiators 38, but as mentioned earlier herein, it could have a chemical biocidal remover 58 in addition to or in place of the irradiators 38.

FIGS. 5A-5G illustrate other views of the system 10 with and without the side panel 15.

FIGS. 6A-6F illustrate another embodiment. In this embodiment like parts are identified with the same part number except that a prime mark ("'") has been added to the part numbers in the embodiments of FIGS. 6A-6F. In this embodiment, the air treatment system 10' comprises a flexible and adjustable gooseneck air hose or duct 20' that comprises a plurality of interconnecting tubular members 52' that are adapted to articulate and pivot relative to each other to provide complete range of motion for the nozzle 26' so that it may be easily positioned in proximity to the patient P. The plurality of segments 52 are interconnected and permit the air hose or duct 20' to articulate universally in any desired direction so that the nozzle 26' may be placed in operative relationship or proximity to the patient P. Thus, it should be appreciated that the air hose or duct 20' defines a universal flexible air hose or duct that is easily manually manipulated in order to change a position of the nozzle 26'. FIGS. 6A-6F illustrate various views of the embodiment of the air treatment system 10' showing different views of the air hose or duct 20'.

In the illustrations being described, it should be appreciated that the nozzle 26, 26' may be removably secured to the inlet end 14, 54' of the air hose or duct 20, 20', respectively. As mentioned earlier herein, the air hose or duct 20, 20' may have a portion that is at least one of flexible, pivotable, extendable or rotatable and that portion may also be semi-rigid. Again, it should be understood that the air hose or duct 20, 20' is flexible and adapted to be repositioned if desired.

ADDITIONAL CONSIDERATIONS

1. As mentioned earlier, a key feature of the embodiments being described is the flexible and articulating gooseneck member or air hose or duct 20 that is at least one of flexible, pivotable, extendable, telescoping or rotatable.

2. Note that the nozzle 26 is generally rectangular at its nozzle end 26a that defines an area A that is larger than the cross-sectional area of the air hose or duct 20. It is contemplated that a filter 77 (FIG. 2C) may be inserted into the nozzle inlet area 26b to provide initial filtration of the airstream. It is also contemplated that the area 12a may comprise one or more additional filtering components, such as a HEPA filter, or include features of one or more of the devices shown in the aforementioned patents which are owned by the same Assignee as the present application.

3. As mentioned earlier, one or more of the air treatment devices 18 may comprise at least one or a plurality of airflow interrupters. The airflow interrupters may comprise a plurality of discrete, randomly oriented and radiation-transmitting objects.

4. While a primary use of the embodiments being described is in an operating room R, it should be understood that the air treatment system 10 is also intended to be used in any environment where it is desired to provide air filtration, such as a triage unit, a room in a building (such as a house or a commercial building) or other area.

5. Note that the airflow generator 28 has been shown and described as a centrifugal blower, it should be understood of course that other types of fans or blowers could be used.

6. In summary, the air treatment device 10 creates a localized negative pressure zone around the patient P within a normal pressure room R. This will have the benefit of allowing the use of regular patient rooms as procedure rooms without requiring patient transportation. It also offers a degree of exposure reduction to personnel within the room R, as pathogens will directly enter the air treatment device 10 and not the ambient room air. The air treatment device 10 is capable of creating a vacuum near the patient and has a filtration system that traps or eliminates air contaminants and an irradiation system that inactivates bacteria.

This invention, including all embodiments shown and described herein, could be used alone or together and/or in combination with one or more of the features covered by one or more of the claims set forth herein, including but not limited to one or more of the features or steps mentioned in the Summary of the Invention and the claims.

While the system, apparatus and method herein described constitute preferred embodiments of this invention, it is to be understood that the invention is not limited to this precise system, apparatus and method, and that changes may be made therein without departing from the scope of the invention which is defined in the appended claims.

What is claimed is:

1. An air treatment system for use during a surgical procedure in a room, said air treatment system comprising:
    a housing having an inlet and an outlet;
    an air treatment device located in said housing for at least one of filtering an airflow or irradiating said airflow before it exits said outlet, said air treatment device housing having at least one of an irradiator or a biocidal remover;
    an air hose or duct adapted to be mounted to said housing in communication with said inlet, said air hose or duct having an inlet end for situating in proximity to a patient situated in said room; and
    an airflow generator for mounting in said housing for generating an air stream between said inlet and said outlet and for creating a negative pressure or vacuum in said air hose or duct;
    said airflow generator generating an airflow through said air hose or duct to create a negative pressure around a patient during said surgical procedure; and
    at least one airflow interrupter or baffle that interrupts the airflow so that an airflow velocity of said airflow through said housing is reduced and a linearity of the airflow is interrupted which, in turn, causes the airflow to have an increased dwell time that said airflow is subjected to said at least one of said irradiator or said biocidal remover; and
    wherein when said at least one airflow interrupter or baffle interrupts said airflow through the housing, said airflow passes through said housing non-linearly and substantially simultaneously said airflow velocity of said airflow is reduced, thereby causing said increased dwell time and exposure that said airflow is subjected to decontamination by said at least one of said irradiator or said biocidal remover.

2. The air treatment system as recited in claim 1 wherein said inlet end comprises a removable nozzle that can be moved or adjusted to a predetermined position by a user.

3. The air treatment system as recited in claim 2 wherein said nozzle has a nozzle end having a nozzle inlet area that is greater than a cross sectional area of said air hose or duct where said nozzle is coupled to said air hose or duct.

4. The air treatment system as recited in claim 1 wherein said air hose or duct has at least a portion that is at least one of flexible, pivotable or rotatable.

5. The air treatment system as recited in claim 2 wherein said nozzle is removable or detachable from said air hose or duct and comprises a filter element.

6. The air treatment system as recited in claim 1 wherein air treatment device comprises a chemical or irradiator for inactivating airborne microbes within said air stream as said air stream flows between said inlet and said outlet.

7. The air treatment system as recited in claim 1 wherein said air treatment system is portable.

8. The air treatment system as recited in claim 1 wherein said air treatment device comprises an air filtration system and at least one of a chemical or irradiating biocidal remover for reducing or eliminating unwanted pathogens in said air stream.

9. The air treatment system as recited in claim 1 wherein said air treatment device located in said housing filters said air stream and also irradiates said air stream to at least one of filtering said airflow or irradiating said airflow before it exits said outlet.

10. The air treatment system as recited in claim 8 wherein said air filtration system comprises said at least one airflow interrupter or baffle for interrupting said air stream to facilitate said at least one of said chemical or irradiating biocidal remover, said at least one airflow interrupter reducing at least one of an air velocity of said air stream or a linearity of a flow of said air stream.

11. The air treatment system as recited in claim 10 wherein said air filtration system comprises a plurality of airflow interrupters, said plurality of airflow interrupters comprising a plurality of discrete, randomly oriented and radiation-transmitting objects.

12. The air treatment system as recited in claim 1 wherein said outlet is at least one of adapted to be fitted to a duct in said room or to re-introduce treated air into a surrounding space in said room.

13. The air treatment system as recited in claim 1 wherein said air treatment system is adapted for use in a room that is not an operating room.

14. The air treatment system as recited in claim 1 wherein said airflow generator comprises a centrifugal blower.

15. The air treatment system as recited in claim 1 wherein said air hose or duct is extendable.

16. The air treatment system as recited in claim 1 wherein said air hose or duct is elongated and semi-rigid with a plurality of areas for permitting a position of said inlet end to be situated in proximity to the patient.

17. The air treatment system as recited in claim 1 wherein said air hose or duct is an articulating and flexible gooseneck member.

18. A mobile air treatment device for use with a patient undergoing a procedure, said mobile air treatment device comprising:
a cabinet that comprises wheels and is portable;
a nozzle that is adapted to be positioned in proximity to the patient;
an airflow generator for creating a primary airflow through said cabinet and a vacuum or negative pressure at said nozzle;
an air treatment device located in said cabinet for at least one of filtering an airflow or irradiating said airflow before it exits said cabinet;
at least one airflow interrupter or baffle situated in said cabinet, said at least one airflow interrupter interrupting said airflow so that an airflow velocity of said airflow through said cabinet is reduced and a linearity of the airflow is interrupted which, in turn, causes the airflow to have an increased dwell time that said airflow is subjected to said air treatment device;
wherein when said at least one airflow interrupter or baffle interrupts said airflow through said cabinet, said airflow passes through said cabinet non-linearly and substantially simultaneously said airflow velocity of said airflow is reduced, thereby causing said increased dwell time and exposure that said airflow is subjected to decontamination by said air treatment device;
wherein said air treatment device comprises an air filtration system and at least one of a chemical or irradiating biocidal remover for reducing or eliminating unwanted pathogens in said airflow; and
wherein said air treatment device is located in said cabinet and decontaminates at least a portion of said airflow before it exits an outlet of said cabinet.

19. The mobile air treatment device as recited in claim 18 wherein said cabinet comprises an adjustable duct arm having said nozzle removably mounted thereon and coupling said nozzle to said cabinet, said adjustable duct arm being moveable by a user when positioning said nozzle in proximity to the patient.

20. The mobile air treatment device as recited in claim 19 wherein said cabinet comprises a flexible or semi-rigid hose or duct having an inlet end coupled to said nozzle and an outlet end coupled to said cabinet, said flexible or semi-rigid hose or duct being moveable or adjustable to a predetermined position by a user.

21. The mobile air treatment device as recited in claim 19 wherein said nozzle has a nozzle end having a nozzle inlet area that is greater than a cross sectional area of said adjustable duct arm where said nozzle is coupled to said adjustable duct arm.

22. The mobile air treatment device as recited in claim 19 wherein said adjustable duct arm has at least a portion that is flexible or pivotable.

23. The mobile air treatment device as recited in claim 20 wherein said nozzle is removable or detachable from said adjustable duct arm and comprises a filter element.

24. The mobile air treatment device as recited in claim 18 wherein air treatment device comprises a chemical or irradiator for inactivating airborne microbes within said airflow as said airflow flows between an inlet in said cabinet and said outlet.

25. The mobile air treatment device as recited in claim 18 wherein said air treatment device comprises said at least one airflow interrupter for interrupting said airflow to facilitate said at least one of said chemical or irradiating biocidal remover, said at least one airflow interrupter reducing at least one of an air velocity of said airflow or a linearity of a flow of said airflow.

26. The mobile air treatment device as recited in claim 25 wherein said at least one airflow interrupter or baffle comprises a plurality of airflow interrupters, said plurality of airflow interrupters comprising a plurality of discrete, randomly oriented and radiation-transmitting objects.

27. The mobile air treatment device as recited in claim 18 wherein said cabinet comprises said outlet that is at least one of adapted to be fitted to a duct in a room where the patient is located or to re-introduce treated air into a surrounding space in said room.

28. The mobile air treatment device as recited in claim 18 in combination with a room that is primarily a patient room and not a surgical operating room.

29. The air treatment system as recited in claim 18 wherein said adjustable duct arm is extendable.

30. The air treatment system as recited in claim 18 wherein said adjustable duct arm is elongated and semi-rigid with a plurality of areas for permitting a position of an inlet end to be situated in proximity to the patient.

31. The air treatment system as recited in claim 18 wherein said adjustable duct arm is an articulating and flexible gooseneck member.

\* \* \* \* \*

UNITED STATES PATENT AND TRADEMARK OFFICE
CERTIFICATE OF CORRECTION

| | |
|---|---|
| PATENT NO. | : 11,185,457 B2 |
| APPLICATION NO. | : 16/854026 |
| DATED | : November 30, 2021 |
| INVENTOR(S) | : David Louis Kirschman |

It is certified that error appears in the above-identified patent and that said Letters Patent is hereby corrected as shown below:

On the Title Page

Item [73], delete "AEROBIOTIX, INC." and insert --AEROBIOTIX, LLC-- therefor.

Signed and Sealed this
Twentieth Day of December, 2022

Katherine Kelly Vidal
*Director of the United States Patent and Trademark Office*